US007595304B2

(12) United States Patent
Zhao et al.

(10) Patent No.: US 7,595,304 B2
(45) Date of Patent: Sep. 29, 2009

(54) POLYMERIC OLIGONUCLEOTIDE PRODRUGS

(75) Inventors: Hong Zhao, Edison, NJ (US); Richard B. Greenwald, Somerset, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 10/822,205

(22) Filed: Apr. 9, 2004

(65) Prior Publication Data

US 2004/0235773 A1 Nov. 25, 2004

Related U.S. Application Data

(60) Provisional application No. 60/462,070, filed on Apr. 13, 2003.

(51) Int. Cl.
*A61K 31/70* (2006.01)
*C07H 21/04* (2006.01)

(52) U.S. Cl. ............... 514/44; 536/24.5; 536/23.1

(58) Field of Classification Search ............... None
See application file for complete search history.

(56) References Cited

U.S. PATENT DOCUMENTS

| | | | |
|---|---|---|---|
| 4,904,582 A | 2/1990 | Tullis | |
| 5,703,218 A | 12/1997 | Urdea et al. | |
| 5,707,813 A * | 1/1998 | Dandliker et al. | 435/6 |
| 5,965,119 A | 10/1999 | Greenwald et al. | |
| 6,040,181 A | 3/2000 | Reed | |
| 6,180,095 B1 | 1/2001 | Greenwald et al. | |
| 6,303,569 B1 * | 10/2001 | Greenwald et al. | 514/2 |
| 6,624,142 B2 | 9/2003 | Greenwald et al. | |
| 6,720,306 B2 | 4/2004 | Greenwald et al. | |
| 6,887,906 B1 * | 5/2005 | Teng et al. | 514/784 |
| 7,122,189 B2 | 10/2006 | Zhao et al. | |
| 2002/0183259 A1 | 12/2002 | Choe et al. | |
| 2004/0249178 A1 | 12/2004 | Vargeese et al. | |

OTHER PUBLICATIONS

Saghir Akhtar, Antisense Technology: Selection and Delivery of Optimally Acting Antisense Oligonucleotides, Journal of Drug Targeting, vol. 5, No. 4, pp. 225-234, 1998.

M. Ballico, et al., Triple, MPEG-Conjugated, Helix-Forming Oligonucleotides (TRIPEGXs): . . . , Bioconjugates Chem. 12, pp. 719-725, 2001.

Gian Maria Bonora, et al., Synthesis and Characterization of High-Molecular Mass . . . , Bioconjugate Chem., vol. 8, pp. 793-797, 1997.

G. M. Bonora, et al., Synthesis by High-Efficiency Liquid-Phase (HELP) Method of Oligonucleotides . . . , Biological Procedures Online, vol. 1, No. 1, May 14, 1998.

Gian Maria Bonora, et al., HELP (High Efficiency Liquid Phase) New Oligonucleotide . . . , Nucleic Acids Research, vol. 18, No. 11, pp. 3155-3159, 1990.

Gian Maria Bonora, et al., Antisense Activity of an Anti-HIV Oligonucleotide Conjugated to Linear . . . , Elsevier Science S.A., 11 Farmaco, vol. 53, pp. 634-637, 1998.

Traian V. Chirila, et al., The Use of Synthetic Polymers for Delivery of Therapeutic Antisense . . . , Biomaterials, vol. 23, pp. 321-342, 2002.

Francesco P. Colonna, Large Scale H.E.L.P. Synthesis of Oligodeoxynucleotides . . . , Tetrahedron Letters, vol. 32, No. 27, pp. 3251-3254, 1991.

Andres Jäschke, et al., Automated Incorporation of Polyethylene Glycol Into Synthetic . . . , Tetrahedron Letters, vol. 34, No. 2, pp. 301-304, 1993.

Andres Jäschke, et al., Synthesis and Properties of Oligodeoxyribonucleotide . . . , Nucleic Acids Research, vol. 22, No. 22, pp. 4810-4817, 1994.

Ji Hoon Jeong, et al., Novel Polymer-DNA Hybrid Polymeric Micelles Composed . . . , Bioconjugate Chem, vol. 12, pp. 917-923, 2001.

Takeo Kawaguchi, et al., Stability, Specific Binding Activity, and Plasma Concentration . . . , Biol. Pharm. Bull., vol. 18(3), pp. 474-476, 1995.

E. Liang, et al., Oligonucleotide Delivery: A Cellular Prospective, Department of Pharmaceutics, Pharmazie, vol. 8, 1999.

Valentina Rapozzi, et al., Antigene Effect in K562 Cells of a PEG-Conjugates . . . , Biochemistry, vol. 41, pp. 502-510, 2002.

Burckhard Seelig, et al., Site-Specific Modification of Enzymatically Sythesized RNA: Transcription . . . , Tetrahedron Letters, vol. 38, No. 44, pp. 7729-7732, 1997.

* cited by examiner

*Primary Examiner*—Tracy Vivlemore
(74) *Attorney, Agent, or Firm*—Lucas & Mercanti, LLP

(57) ABSTRACT

Polymer conjugates containing nucleotides and/or oligonucleotides are disclosed.

28 Claims, 12 Drawing Sheets

POLYMERIC OLIGONUCLEOTIDE PRODRUGS

CROSS-REFERENCE TO RELATED APPLICATIONS

This application claims the benefit of priority from U.S. Provisional Patent Application Ser. No. 60/462,070, filed Apr. 13, 2003, the contents of which are incorporated herein by reference.

FIELD OF THE INVENTION

The present inventions relates to polymeric oligonucleotide prodrugs useful as therapeutic agents. Compositions and methods of using such prodrugs are also provided.

BACKGROUND

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics have generally focused upon interactions with such proteins in efforts to moderate their disease-causing or disease potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides that are complementary to a specific target messenger RNA (mRNA) sequence. Generally, nucleic acid sequences complementary to the products of gene transcription (e.g., mRNA) are designated "antisense", and nucleic acid sequences having the same sequence as the transcript or being produced as the transcript are designated "sense". See, e.g., Crooke, 1992, *Annu. Rev. Pharmacol. Toxicol.*, 32: 329-376. An antisense oligonucleotide can be selected to hybridize to all or part of a gene, in such a way as to modulate expression of the gene. Transcription factors interact with double-stranded DNA during regulation of transcription. Oligonucleotides can serve as competitive inhibitors of transcription factors to modulate their action. Several recent reports describe such interactions (see Bielinska, A., et al., 1990, *Science*, 250: 997-1000; and Wu, H., et al., 1990, *Gene* 89: 203-209).

Molecular strategies are being developed to down-regulate unwanted gene expression. Recently, the use of modified oligonucleotide compounds has developed into a promising method of treatment against such diseases as viral infections, inflammatory and genetic disorder and significantly, cancer. Antisense DNAs were first conceived as alkylating complementary oligodeoxynucleotides directed against naturally occurring nucleic acids (Belikova, et al., *Tetrahedron Lett.* 37:3557-3562, 1967). Zamecnik and Stephenson were the first to propose the use of synthetic antisense oligonucleotides for therapeutic purposes. (Zamecnik & Stephenson, 1978, *Proc. Natl. Acad. Sci. U.S.A.*, 75:285-289; Zamecnik & Stephenson, 1978, *Proc. Natl. Acad. Sci. U.S.A.*, 75:280-284). They reported that the use of an oligonucleotide 13-mer complementary to the RNA of Rous sarcoma virus inhibited the growth of the virus in cell culture. Since then, numerous other studies have been published manifesting the in vitro efficacy of antisense oligonucleotide inhibition of viral growth, e.g., vesicular stomatitis viruses (Leonetti et al., 1988, *Gene*, 72:323), herpes simplex viruses (Smith et al., 1987, *Proc. Natl. Acad. Sci. U.S.A.* 83:2787), and influenza virus (Seroa; et al., 1987, *Nucleic Acids Res.* 15:9909).

Oligonucleotides have also found use in among others, diagnostic tests, research reagents e.g. primers in PCR technology and other laboratory procedures. Oligonucleotides can be custom synthesized to contain properties that are tailored to fit a desired use. Thus numerous chemical modifications have been introduced into oligomeric compounds to increase their usefulness in diagnostics, as research reagents and as therapeutic entities.

Although oligonucleotides, especially antisense oligonucleotides show promise as therapeutic agents, they are very susceptible to nucleases and can be rapidly degraded before and after they enter the target cells making unmodified antisense oligonucleotides unsuitable for use in in vivo systems. Because the enzymes responsible for the degradation are found in most tissues, modifications to the oligonucleotides have been made in an attempt to stabilize the compounds and remedy this problem. The most widely tested modifications have been made to the back-bone portion of the oligonucleotide compounds. See generally Uhlmann and Peymann, 1990, *Chemical Reviews* 90, at pages 545-561 and references cited therein. Among the many different back bones made, only phosphorothioate showed significant antisense activity. See for example, Padmapriya and Agrawal, 1993, *Bioorg. & Med. Chem. Lett.* 3, 761. While the introduction of sulfur atoms to the back bone slows the enzyme degradation rate, it also increases toxicity at the same time. Another disadvantage of adding sulfur atoms is that it changes the back bone from achiral to chiral and results in $2^n$ diastereomers. This may cause further side effects. Still more disadvantages of present antisense oligonucleotides are that they may carry a negative charge on the phosphate group which inhibits its ability to pass through the mainly lipophilic cell membrane. The longer the compound remains outside the cell, the more degraded it becomes resulting in less active compound arriving at the target. A further disadvantage of present antisense compounds is that oligonucleotides tend to form secondary and high-order solution structures. Once these structures are formed, they become targets of various enzymes, proteins, RNA, and DNA for binding. This results in nonspecific side effects and reduced amounts of active compound binding to mRNA. Other attempts to improve oligonucleotide therapy have included adding a linking moiety and polyethylene glycol. See for example, Kawaguchi, et al., Stability, Specific Binding Activity, and Plasma Concentration in Mice of an Oligodeoxynucleotide Modified at 5'-Terminal with Poly (ethylene glycol), *Biol. Pharm. Bull.*, 18(3) 474-476 (1995), and U.S. Pat. No. 4,904,582. In both of these examples, the modifications involve the use of linking moieties that are permanent in nature in an effort to stabilize the oligonucleotide against degradation and increase cell permeability. However, both of these efforts fail to provide any efficacy.

Due to the inadequacies of the present methods, there exists a need to improve stability and resistance to nuclease degradation as well as decrease toxicity and increase binding affinity to mRNA of oligonucleotide compounds. The current oligonucleotide therapy is expensive. This is mainly due to the degradation problem. Thus, there is a real need to protect the antisense oligonucleotide compounds against degradation, prevent the formation of high-order structures and at the same time deliver sufficient amounts of active antisense oligonucleotide compounds to the target. This invention provides such improvements.

SUMMARY OF THE INVENTION

In one aspect of the invention there are provided oligonucleotide prodrugs of formula (I):

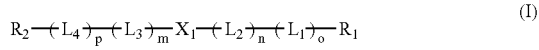

wherein:
$R_1$ and $R_2$ are independently H or a polymer residue;
$L_1$ and $L_4$ are independently selected releasable linking moieties;
$L_2$ and $L_3$ are independently selected spacing groups;
$X_1$ is a nucleotide residue or an oligonucleotide residue;
m, n, o and p are independently zero or a positive integer, provided that either (o+n) or (p+m)≧2.

Another aspect of the invention includes bifunctional compounds that are formed when $R_1$ and/or $R_2$ are polymer residues which include both an alpha and an omega terminal linking group as described herein so that two oligonucleotides are linked to the polymeric delivery systems provided. Examples of this embodiment include oligonucleotides joined to the polymer systems through their respective 3'-, 5'-terminal groups, e.g. 3'-bis oligonucleotide conjugates or 5'-bis oligonucleotide conjugates, or a conjugate formed by linking a first oligonucleotide via the 3'-terminal to the 5'-terminal of a second oligonucleotide. Examples of such polymer conjugates are illustrated below as formulas (i), (ii), (iii) and (iv):

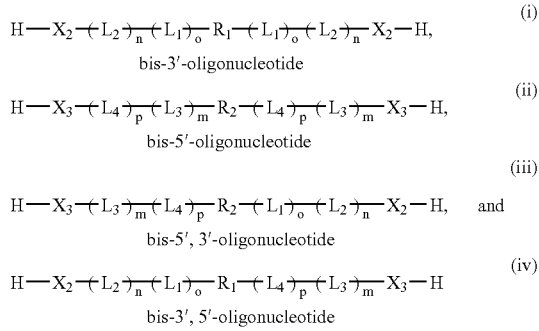

wherein all variables are as described above.

For purposes of the present invention, the term "residue" shall be understood to mean that portion of a biologically active compound i.e. an oligonucleotide, more specifically an antisense oligonucleotide, which remains after it has undergone a substitution reaction in which the prodrug carrier has been attached.

For purposes of the present invention, the term "polymeric residue" or "PEG residue" shall each be understood to mean that portion of the polymer or PEG which remains after it has undergone a reaction with a modified oligonucleotide compound.

For purposes of the present invention, the term "alkyl" shall be understood to include straight, branched, substituted, e.g. halo-, alkoxy-, nitro-, $C_{1-12}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo- shall be understood to include fluoro, chloro, iodo and bromo.

The term "sufficient amounts" or "effective amounts" for purposes of the present invention shall mean an amount which achieves a therapeutic effect as such effect is understood by those of ordinary skill in the art.

Some of the chief advantages of the present invention include novel polymeric oligonucleotide prodrugs that demonstrate increased stability and resistance to nuclease degradation, increased solubility, increased cell permeability and decreased toxicity.

Another advantage of the compounds of the invention is that a variety of polymeric prodrug platforms are releasably attached to the modified oligonucleotide compounds. This advantage allows for the artisan to design a drug conjugate that can be manipulated to include various moieties between the polymeric residue and the attached oligonucleotide that can effect the rate of hydrolysis of the prodrug. The artisan thus has the ability to include substituents that allow for modulation of the rate of hydrolysis of the prodrug.

Methods of making and using the compounds, such as in methods of treating cancers or malignancies, and conjugates described herein are also provided. It is also contemplated that inventive polymeric oligonucleotide prodrugs be administered together with (simultaneously and/or sequentially) any other suitable anticancer agent.

DETAILED DESCRIPTION OF THE INVENTION

Figure 1:
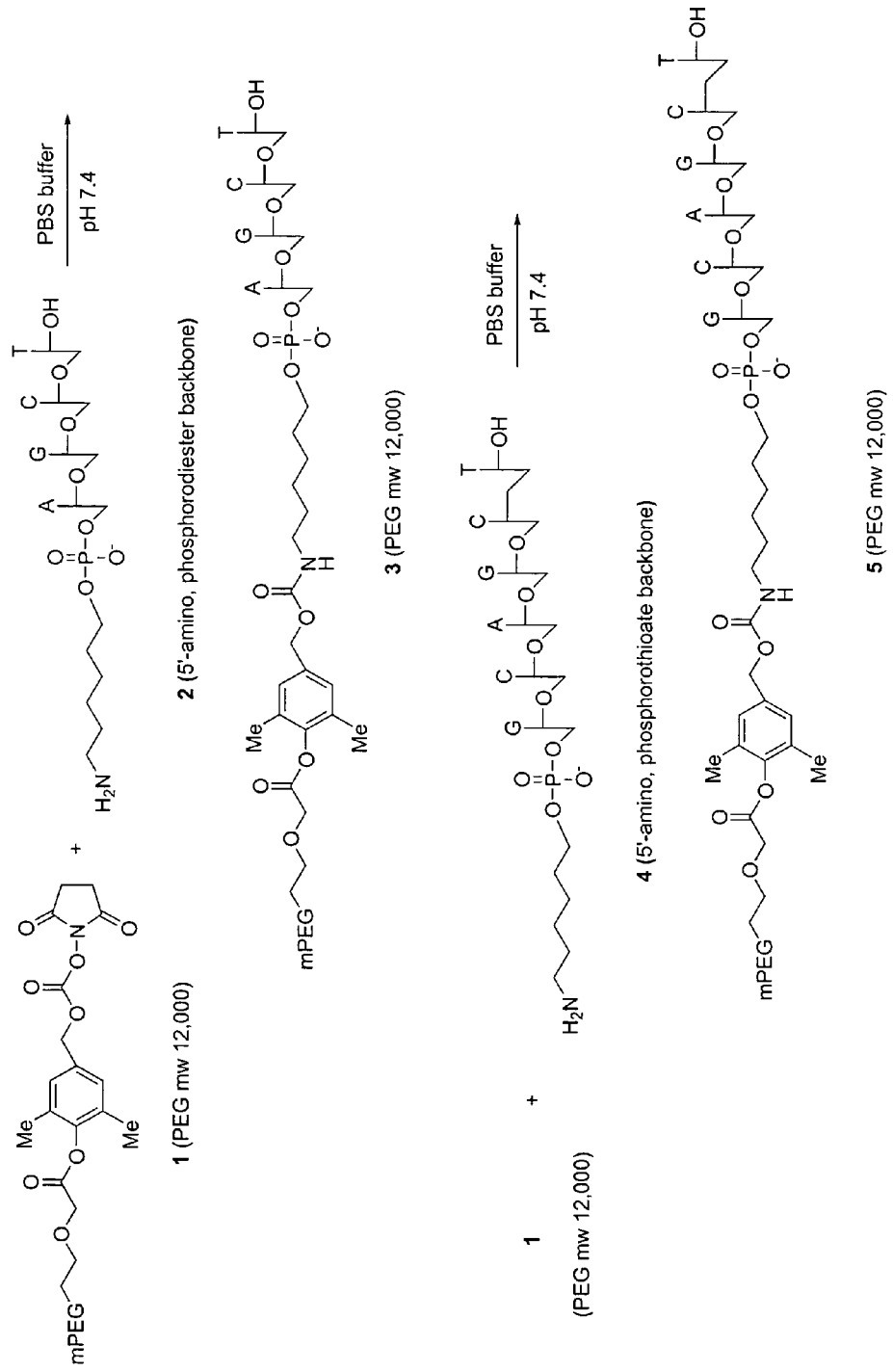
FIG. 1 schematically illustrates methods of preparing the PEGylated oligonucleotides of compounds 3 and 5.
Figure 2:
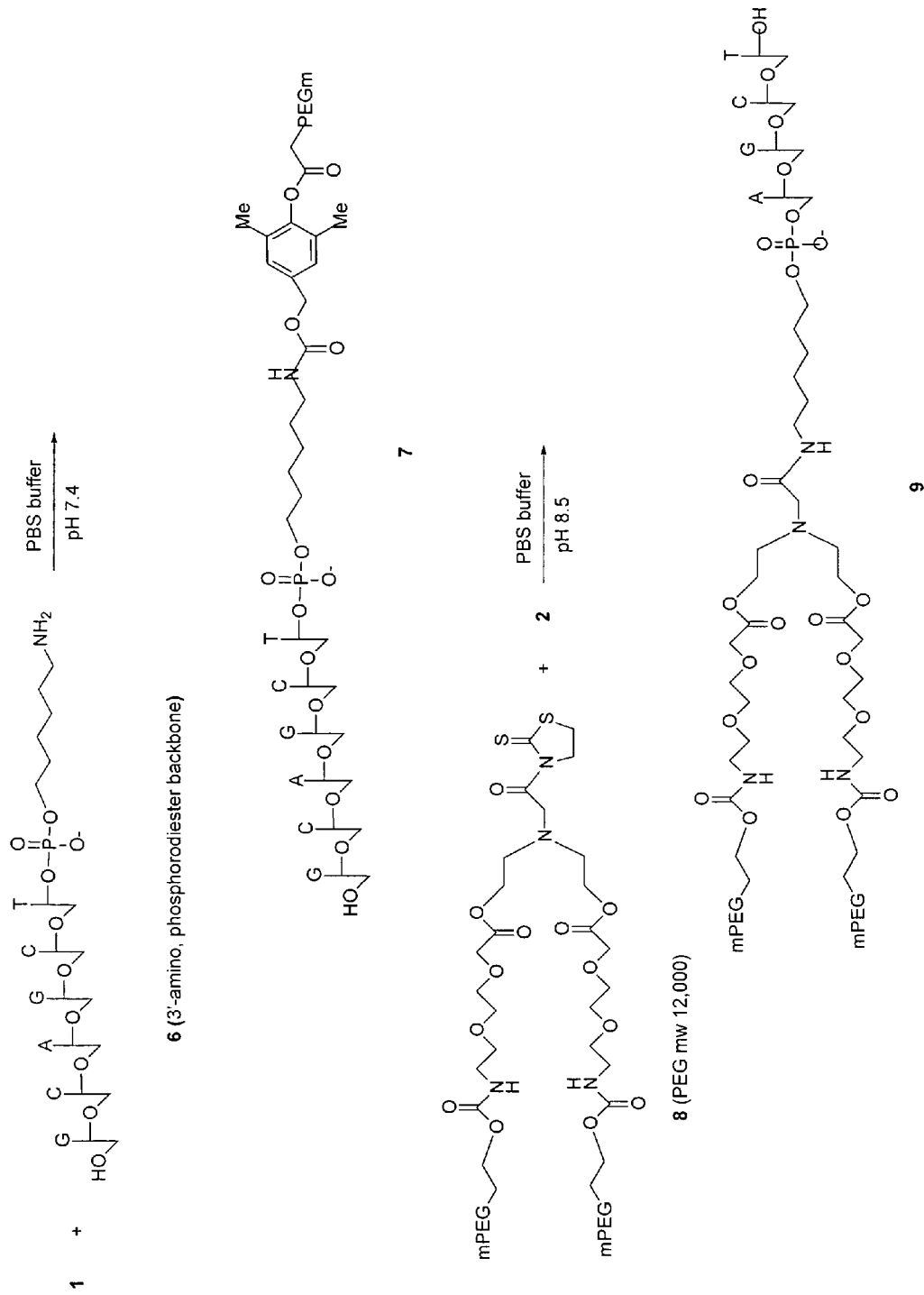
FIG. 2 schematically illustrates methods of preparing the PEGylated oligonucleotides of compounds 7 and 9.
Figure 3:
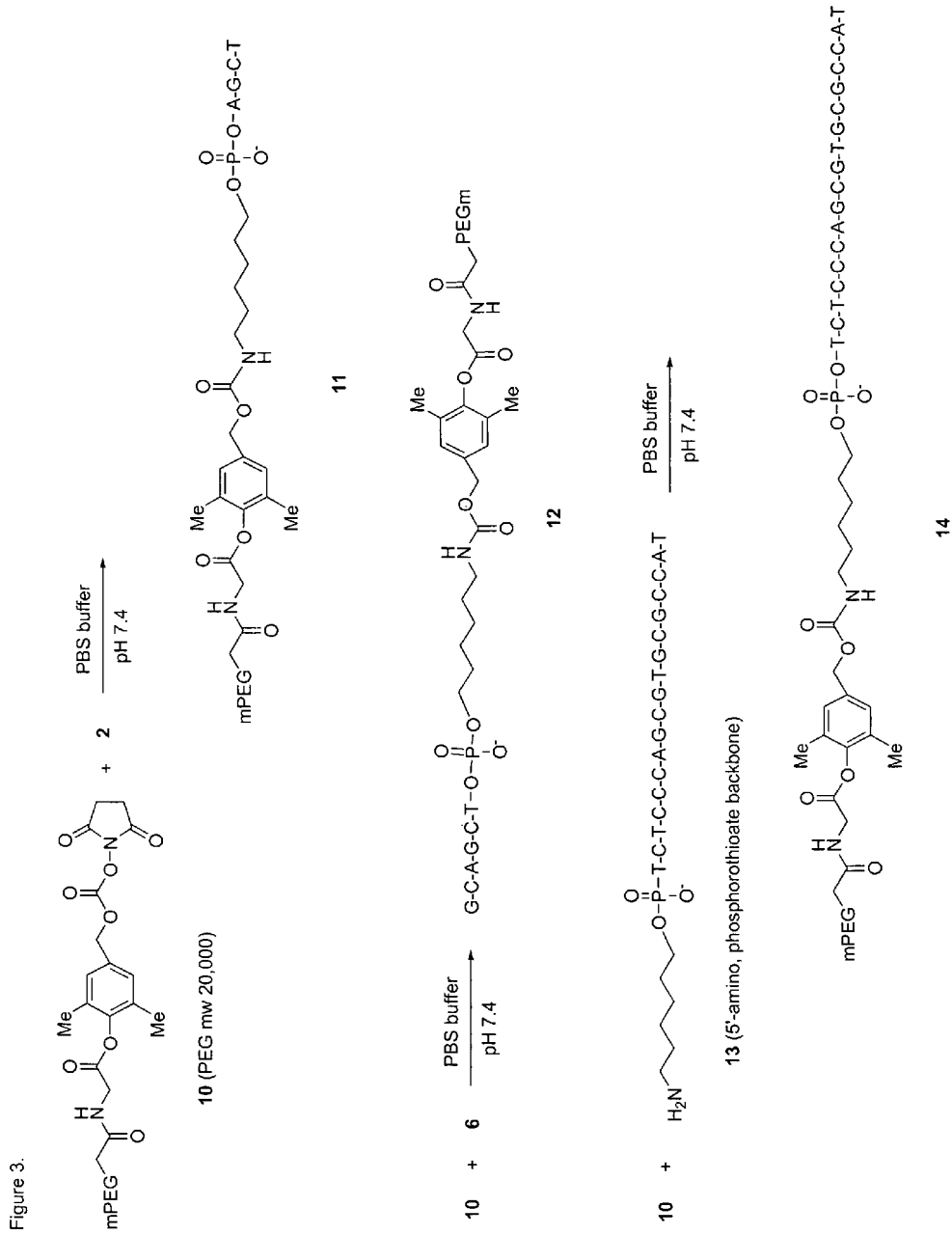
FIG. 3 schematically illustrates methods of preparing the PEGylated oligonucleotides of compounds 11, 12 (SEQ ID NO: 1) and 14 (SEQ ID NO: 1).
Figure 4:
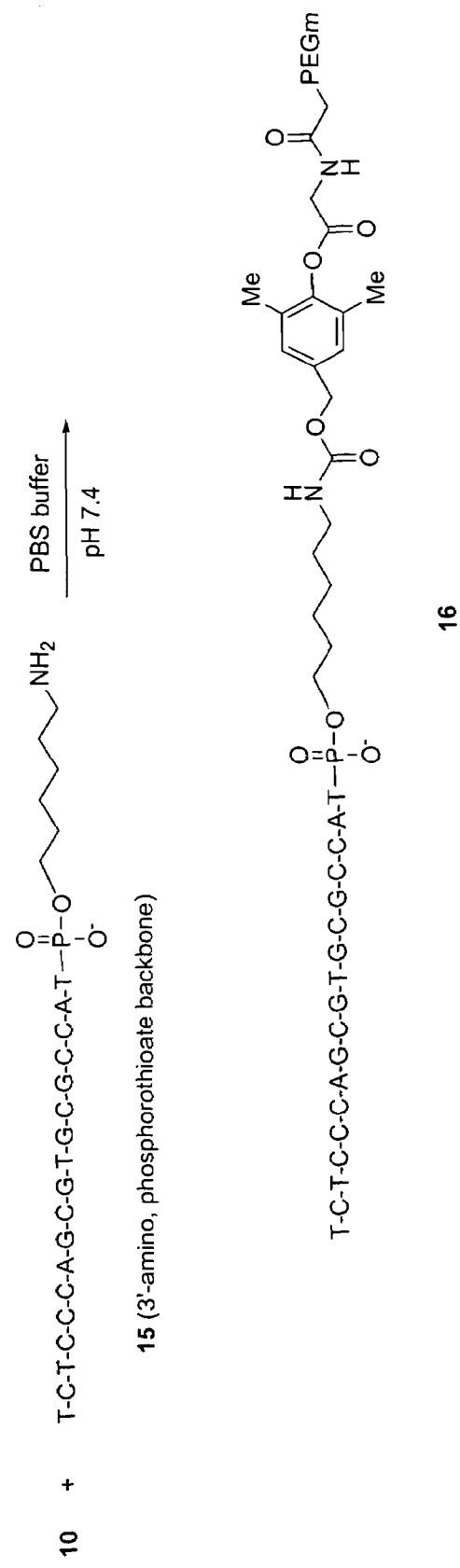
FIG. 4 schematically illustrates a method of preparing the PEGylated oligonucleotide of compound 16 (SEQ ID NO: 1).
Figure 5:
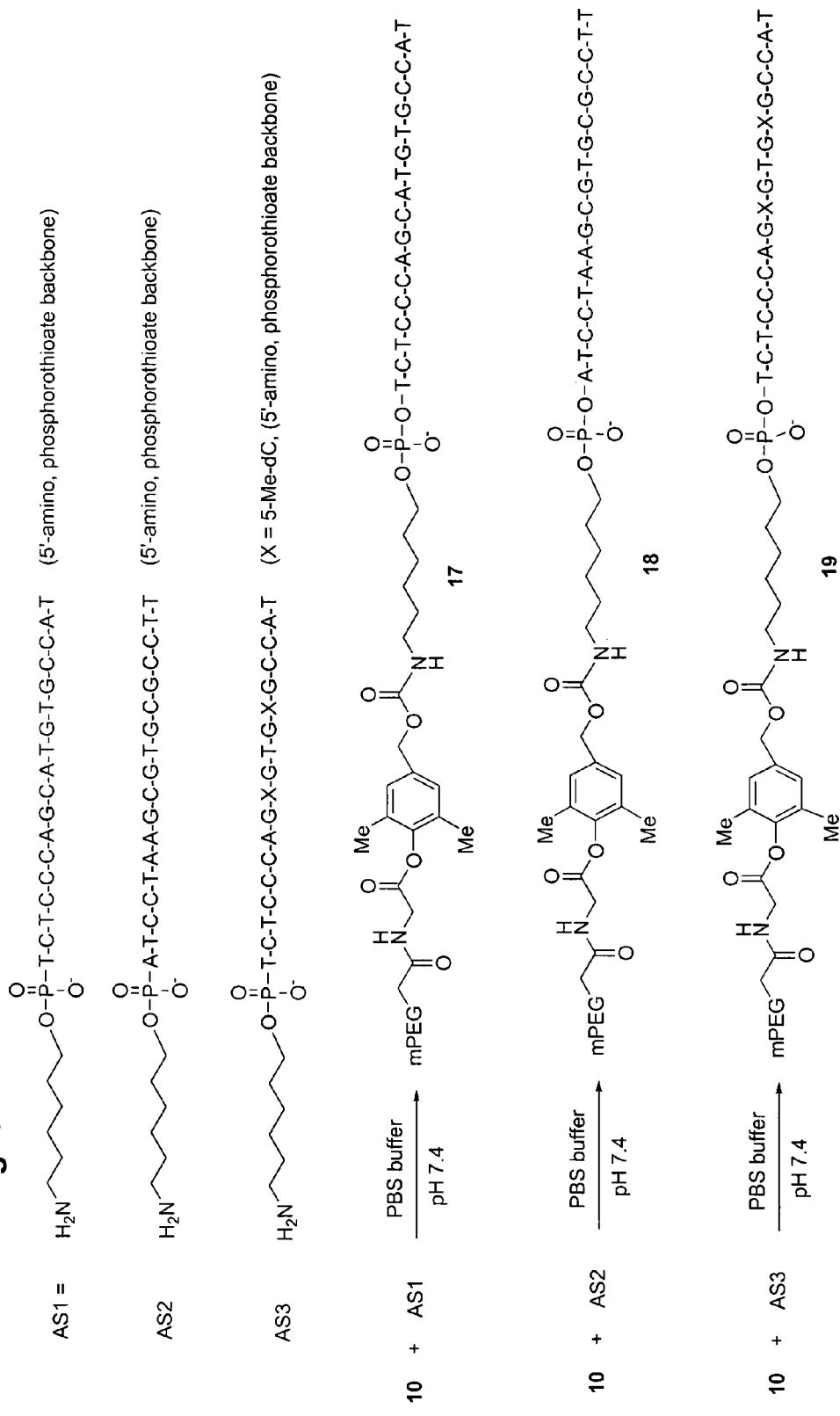
FIG. 5 schematically illustrates methods of preparing the PEGylated oligonucleotides of compounds 17 (SEQ ID NO: 2), 18 (SEQ ID NO: 3) and 19 (SEQ ID NO: 4), from AS1 (SEQ ID NO:2), AS2 (SEQ ID NO:3) and AS3 (SEQ ID NO:4).
Figure 6:
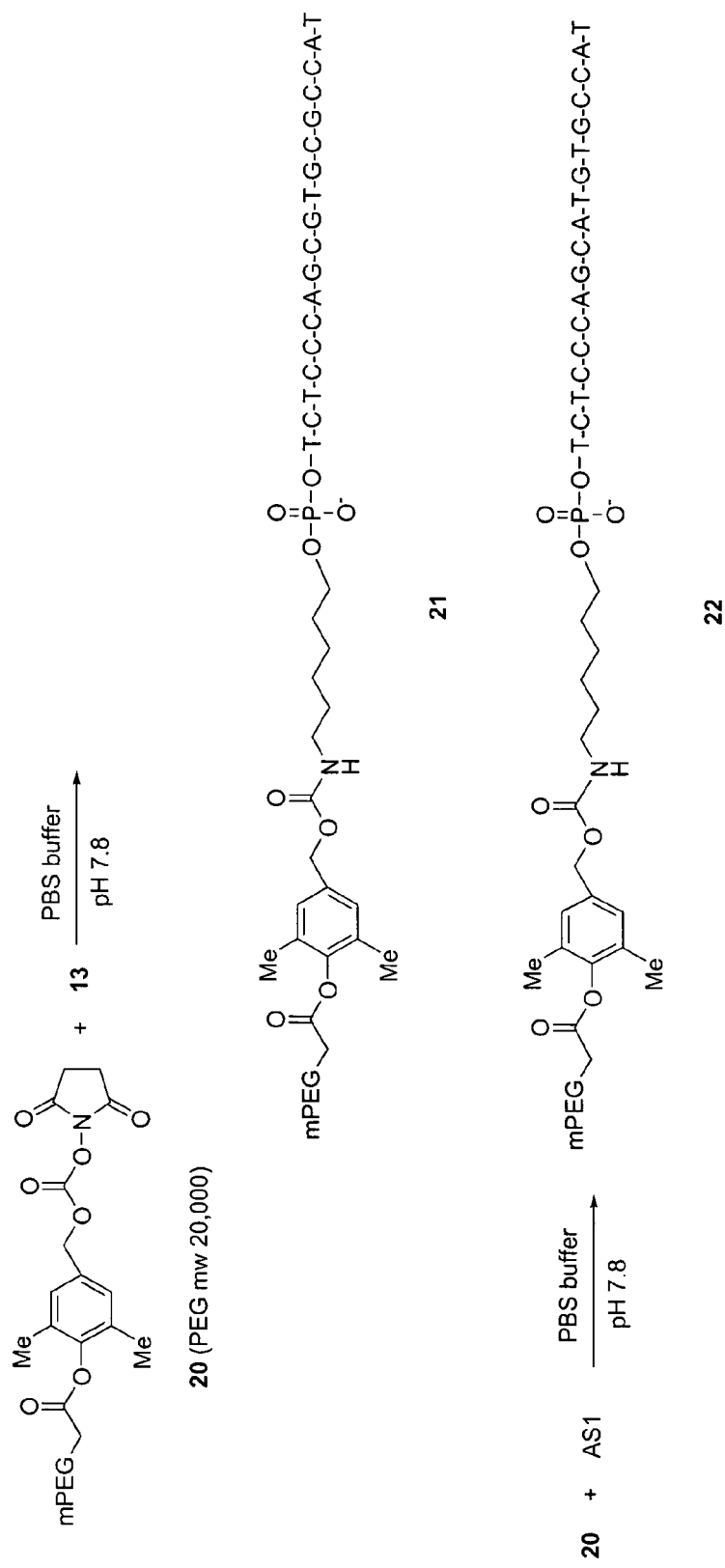
FIG. 6 schematically illustrates methods of preparing the PEGylated oligonucleotides of compounds 21 (SEQ ID NO: 1) and 22 (SEQ ID NO: 2).
Figure 7:
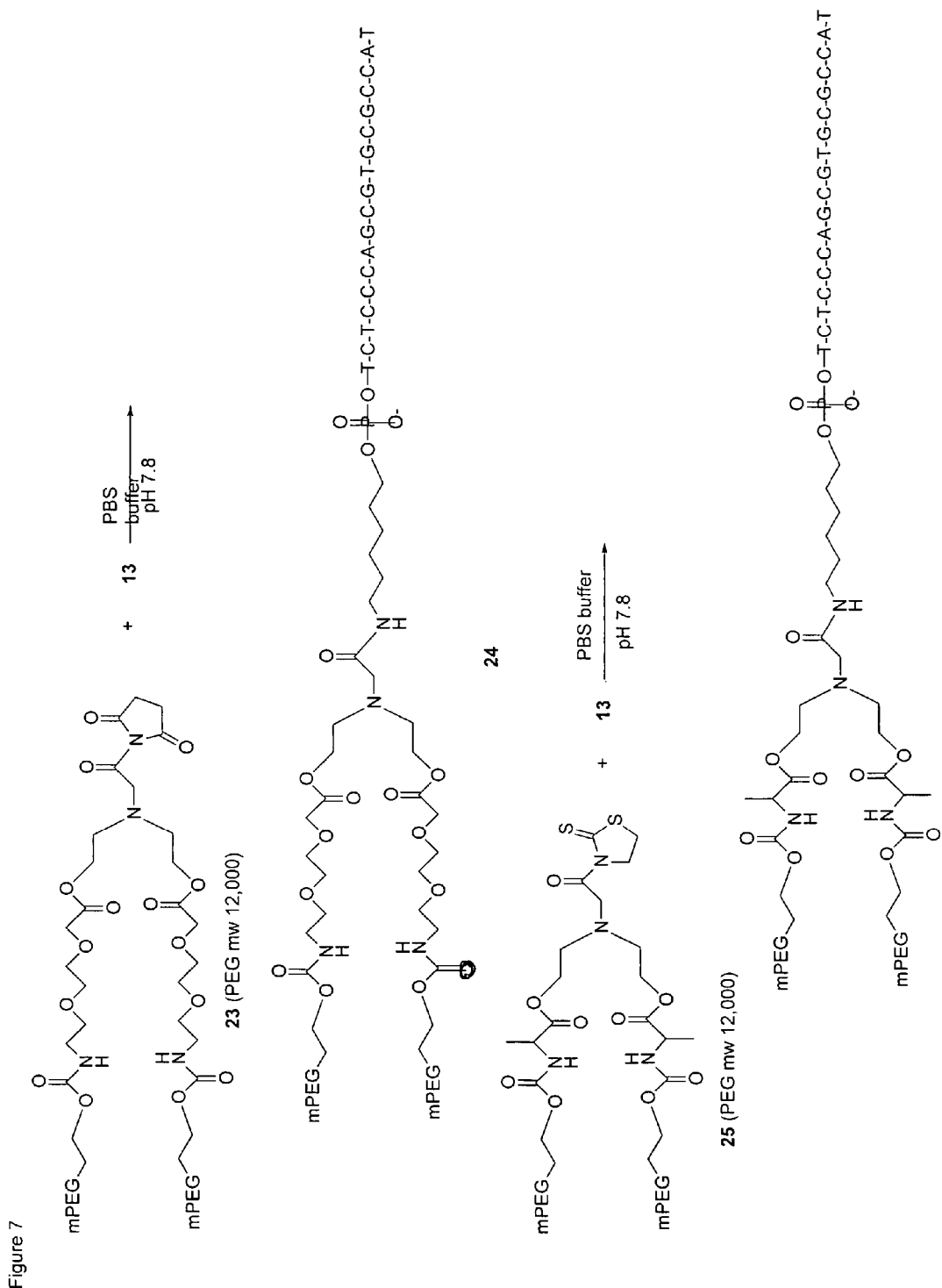
FIG. 7 schematically illustrates methods of preparing the PEGylated oligonucleotides of compounds 24 (SEQ ID NO: 1) and 26 (SEQ ID NO: 1).
Figure 8:
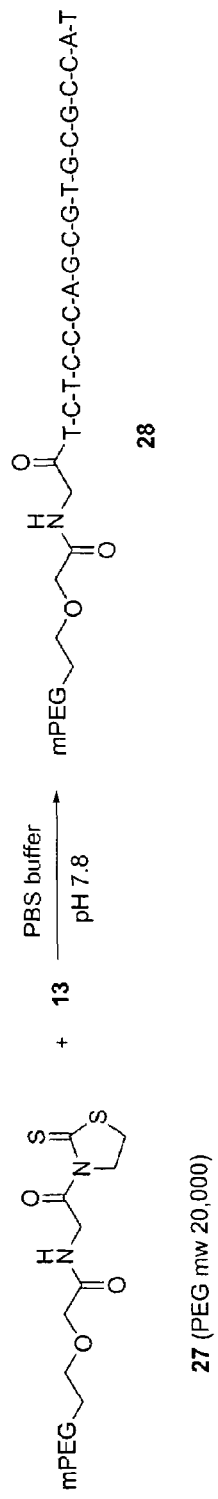
FIG. 8 schematically illustrates methods of preparing the PEGylated oligonucleotides of compounds 28 (SEQ ID NO: 1), 29 (SEQ ID NO: 2), 30 (SEQ ID NO: 3) and 31 (SEQ ID NO: 4), from AS1 (SEQ ID NO:2), AS2 (SEQ ID NO:3) and AS3 (SEQ ID NO:4).
Figure 9:
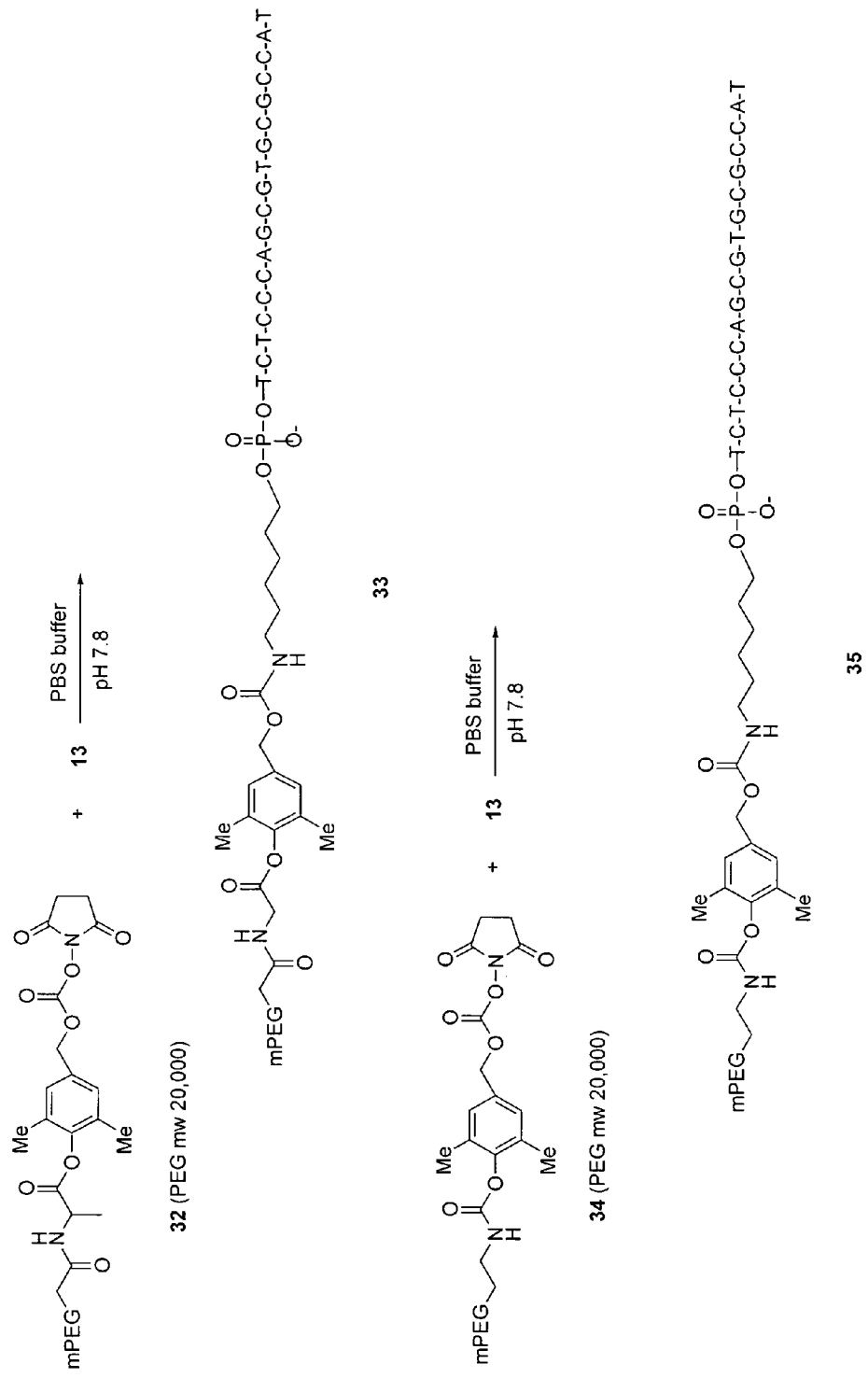
FIG. 9 schematically illustrates methods of preparing the PEGylated oligonucleotides of compounds 33 (SEQ ID NO: 1) and 35 (SEQ ID NO: 1).

Accordingly, the present invention provides for polymer-linked oligonucleotide prodrugs useful having many practical uses, including uses as diagnostic and analytic reagents, as research and investigational tools, both in vitro and in vivo, and as therapeutic agents. In order to more fully appreciate the scope of the present invention, the following terms are defined. The artisan will appreciate that the terms, "nucleic acid" or "nucleotide" apply to deoxyribonucleic acid ("DNA"), ribonucleic acid, ("RNA") whether single-stranded or double-stranded, unless otherwise specified, and any chemical modifications thereof. An "oligonucleotide" is generally a relatively short polynucleotide, e.g., ranging in size from about 2 to about 200 nucleotides, or more preferably from about 10 to about 30 nucleotides in length. The oligonucleotides according to the invention are generally synthetic nucleic acids, and are single stranded, unless otherwise specified. The terms, "polynucleotide" and "polynucleic acid" may also be used synonymously herein.

Modifications to the oligonucleotides of the invention optionally include, for example, the addition to or substitution of selected nucleotides with functional groups or moieties that permit covalent linkage of an oligonucleotide to a desirable polymer, and/or the addition or substitution of functional moieties that incorporate additional charge, polarizability, hydrogen bonding, electrostatic interaction, and functionality to an oligonucleotide. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications, methylations, base-pairing combinations such as the isobases isocytidine and isoguanidine, and analogous combinations. Oligonucleotide modifications can also include 3' and 5' modifications such as capping.

The term "antisense," as used herein, refers to nucleotide sequences which are complementary to a specific DNA or RNA sequence that encodes a gene product or that encodes a control sequence. The term "antisense strand" is used in reference to a nucleic acid strand that is complementary to the "sense" strand. In the normal operation of cellular metabolism, the sense strand of a DNA molecule is the strand that encodes polypeptides and/or other gene products. The sense strand serves as a template for synthesis of an messenger RNA ("mRNA") transcript (an antisense strand) which, in turn, directs synthesis of any encoded gene product. Antisense nucleic acid molecules may be produced by any art-known methods, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designations "negative" or (−) are also art-known to refer to the antisense strand, and "positive" or (+) are also art-known to refer to the sense strand For example, if it is intended to downregulate expression of an mRNA transcript in a cell or cells, the antisense oligonucleotide is introduced into a cell. Once introduced into a cell, the antisense oligonucleotide hybridizes to the corresponding mRNA sequence through Watson-Crick binding, forming a heteroduplex. Once the duplex is formed, translation of the protein coded by the sequence of bound mRNA is inhibited. Thus, antisense oligonucleotides are also employed in the art as probes, e.g., hybridization probes, generally linked to a tag or label, as well as being used to provide precise downregulation of the expression of specific cellular products or genetic regulatory elements for both investigational and therapeutic purposes.

For purposes of the present invention, the use of the singular or plural is not meant to be limiting of the numerical number of the referenced item or object. Thus, the use of the singular to refer to a cell, polymer or drug does not imply that only one cell is treated, only one molecule is prepared or employed, and/or only one drug is employed, and the use of the plural does not exclude application to a single referenced item, unless expressly stated.

For purposes of the present invention, the term "residue" shall be understood to mean that portion of a biologically active compound, such as an oligonucleotide, which remains after it has undergone a reaction in which the prodrug carrier portion has been attached by modification of e.g., an available hydroxyl or amino group, to form, for example, an ester or amide group, respectively.

A. Description of the Oligonucleotides

One of the features of the invention is the ability to provide improved nucleotide or oligonucleotide polymer conjugates. The polymer transport systems described herein are not limited to a single species of oligonucleotide but, instead, are designed to work with a wide variety of such moieties, it being understood that the polymer transport systems can attach to one or more of the 3'- or 5'-terminals, usually $PO_4$ or $SO_4$ groups of a nucleotide. The nucleotide sequences are depicted herein using conventional nomenclature, wherein the sequences are read from left to right, going from the 5'-terminus to the 3'-terminus (5'-→3'-).

$X_{1-3}$ represent the same or different nucleotide or oligonucleotide residue, which for purposes of the present invention include oligodeoxynucleotide residues. More preferably, $X_{1-3}$ are independently selected antisense oligonucleotide residues or antisense oligodeoxynucleotide residues.

A non-limiting list of potential nucleotides which can be used either alone or as part of an oligonucleotide (10-1,000 nucleotides) include

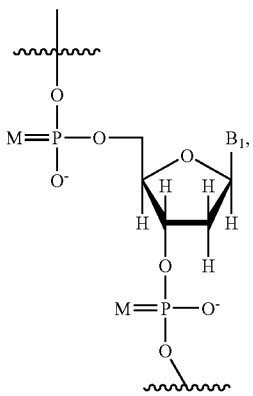

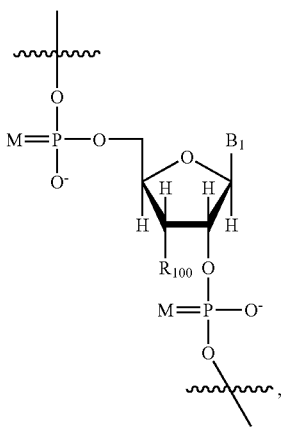

-continued

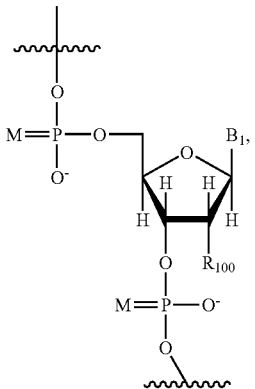

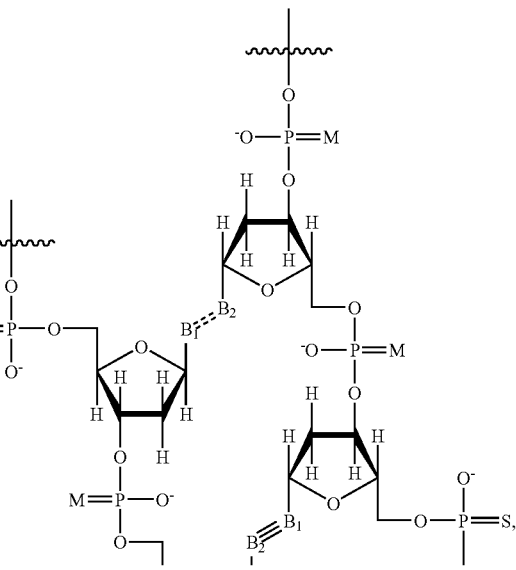

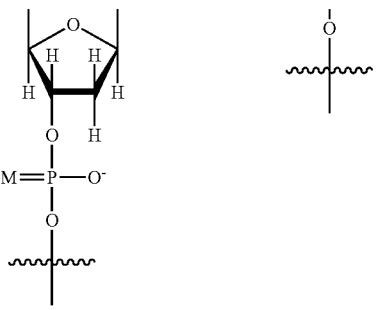

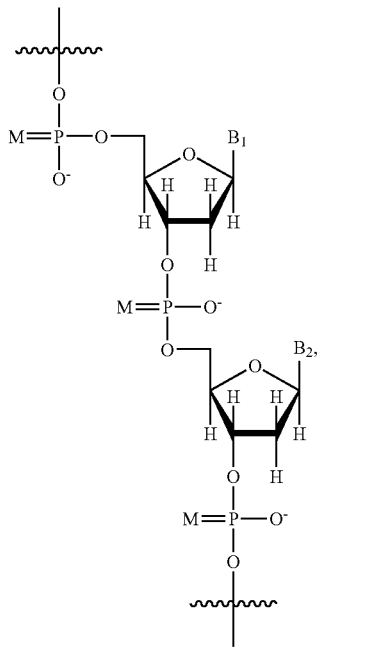
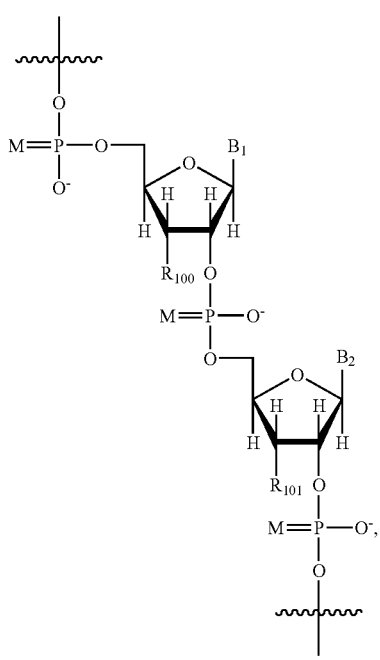
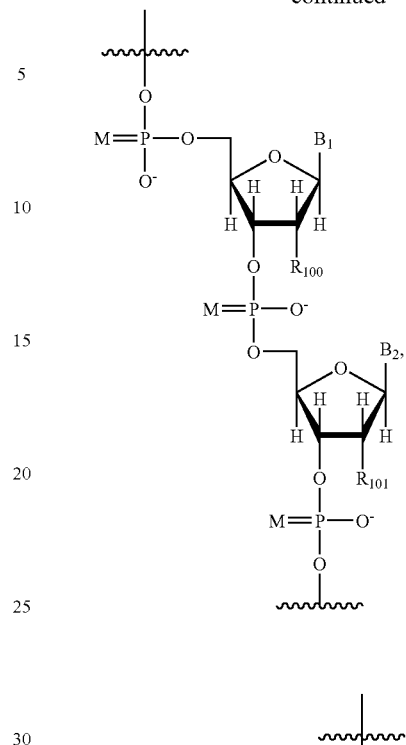
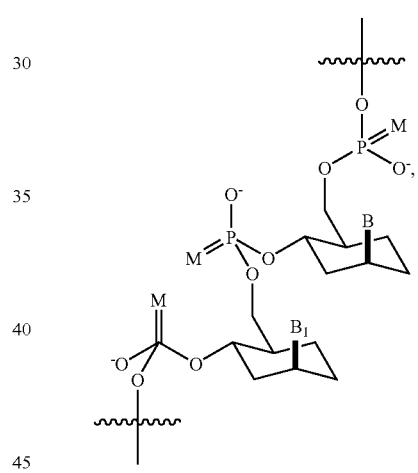
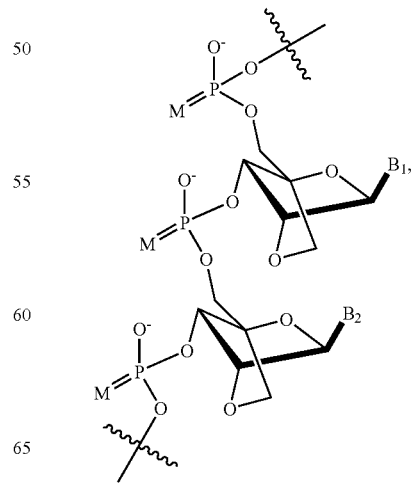

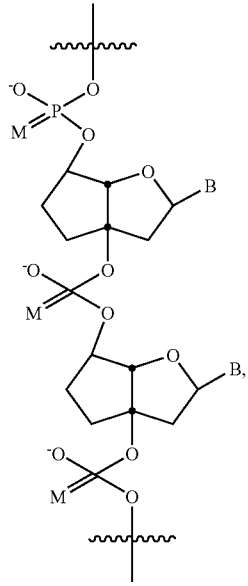

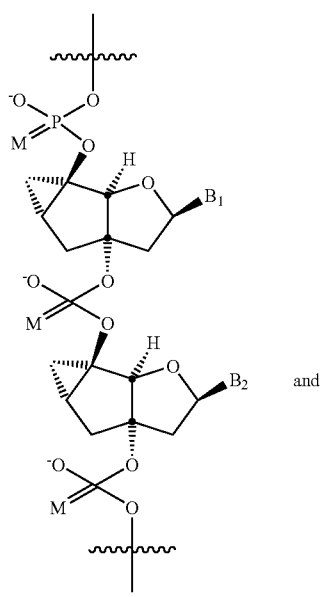
and

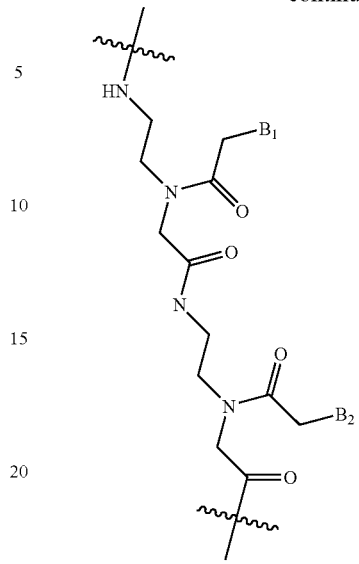

wherein

M is O or S;

$B_1$ and $B_2$ are independently selected from the group consisting of A (adenine), G (guanine), C (cytosine), T (thymine), U (uracil) and modified bases, including those shown below and those known to those of ordinary skill;

$R_{100}$ and $R_{101}$ are independently selected from the group consisting of H, OR' where R' is H, a $C_{1-6}$ alkyl, substituted alkyl, nitro, halo, aryl, etc.

Some of the oligonucleotides and oligodeoxynucleotides useful in the methods of the invention include, but are not limited to, the following:

Oligonucleotides and oligodeoxynucleotides with natural phosphorodiester backbone or phosphorothioate backbone or any other modified backbone analogues;

LNA (Locked Nucleic Acid);

PNA (nucleic acid with peptide backbone);

tricyclo-DNA;

decoy ODN (double stranded oligonucleotide);

RNA (catalytic RNA sequence);

ribozymes;

spiegelmers (L-conformational oligonucleotides);

CpG oligomers, and the like, such as those disclosed at:

Tides 2002, Oligonucleotide and Peptide Technology Conferences, May 6-8, 2002, Las Vegas, Nev. and Oligonucleotide & Peptide Technologies, 18th & 19th Nov. 2003, Hamburg, Germany, the contents of which are incorporated herein by reference.

Oligonucleotides according to the invention can also optionally include any suitable art-known nucleotide analogs and derivatives, including those listed by Table 1, below.

TABLE 1

Representative Nucleotide Analogs And Derivatives

| | |
|---|---|
| 4-acetylcytidine | 5-methoxyaminomethyl-2-thiouridine |
| 5-(carboxyhydroxymethyl)uridine | beta, D-mannosylqueuosine |
| 2'-O-methylcytidine | 5-methoxycarbonylmethyl-2-thiouridine |

TABLE 1-continued

Representative Nucleotide Analogs And Derivatives

| | |
|---|---|
| 5-carboxymethylaminomethyl-2-thiouridine | 5-methoxycarbonylmethyluridine |
| 5-carboxymethylaminomethyluridine | 5-methoxyuridine |
| Dihydrouridine | 2-methylthio-N6-isopentenyladenosine |
| 2'-O-methylpseudouridine | N-((9-beta-D-ribofuranosyl-2-methylthiopurine-6-yl)carbamoyl)threonine |
| D-galactosylqueuosine | N-((9-beta-D-ribofuranosylpurine-6-yl)N-methylcarbamoyl)threonine |
| 2'-O-methylguanosine | uridine-5-oxyacetic acid-methylester |
| Inosine | uridine-5-oxyacetic acid |
| N6-isopentenyladenosine | wybutoxosine |
| 1-methyladenosine | pseudouridine |
| 1-methylpseudouridine | queuosine |
| 1-methylguanosine | 2-thiocytidine |
| 1-methylinosine | 5-methyl-2-thiouridine |
| 2,2-dimethylguanosine | 2-thiouridine |
| 2-methyladenosine | 4-thiouridine |
| 2-methylguanosine | 5-methyluridine |
| 3-methylcytidine | N-((9-beta-D-ribofuranosylpurine-6-yl)-carbamoyl)threonine |
| 5-methylcytidine | 2'-O-methyl-5-methyluridine |
| N6-methyladenosine | 2'-O-methyluridine |
| 7-methylguanosine | wybutosine |
| 5-methylaminomethyluridine | 3-(3-amino-3-carboxy-propyl)uridine |

Preferably, the antisense oligonucleotide is one that downregulates a protein implicated in the resistance of tumor cells to anticancer therapeutics. For example, the protein BCL-2 inhibits the release of Cytochrome-C and Apoptosis Initiating Factor from mitochondria and thus prevents apoptosis from occurring. Cancer cells that have high levels of BCL-2 are thus very resistant to both chemotherapy or radiation therapy. U.S. Pat. No. 6,414,134, incorporated by reference herein, describes antisense oligonucleotides that downregulate the protein Bcl-2 that is associated with resistance to anticancer therapy in a number of tumor cells, e.g., including prostate cancer cells, myeloma cells and other tumor cells. According to the above-noted U.S. patent, the bcl-2 gene is believed to contribute to the pathogenesis of cancer primarily by prolonging tumor cell survival rather than by accelerating cell division. U.S. Pat. No. 6,414,134 generally describes antisense oligonucleotides of 17 to 35 bases in length, that are complementary to bcl-2 mRNA, and that include a nucleic acid molecule having the sequence of TACCGCGTGC GAC-CCTC (SEQ ID NO: 5). These preferably include at least one phosphorothioate linkage.

Other art-known cellular proteins that are contemplated by various companies as targets for downregulation by antisense oligonucleotides, for cancer therapy, are summarized by the following table.

TABLE 2

| Antisense Agent | Target Protein |
|---|---|
| Affinitak (ISIS 3521) | PKC-alpha |
| ISIS 112989 (OGX 011) | Secretory Protein Clusterin |
| ISIS 23722 | Survivin |
| AP 12009 | TGF-Beta2 |
| GEM 231 | Protein kinase A |
| GEM 240 | MDM2 |
| IGF-1R/AS ODN | Insulin-like growth factor |
| MG98 | DNA methyltransferase |
| LErafAON | C-raf-1 |
| Ki-67 antisense oligonucleotide | Ki-67 |
| GTI-2040 | ribonucleotide reductase |
| ISIS 2503 | H-ras |
| AP11014 | TGF-Beta1 |

Antisense oligonucleotides suitable for use in downregulating the expression of proteins related to cancer cell survival, such as bcl-2 expression include oligonucleotides that are from about two to two hundred nucleotide codons; more preferably ten to forty codons; and most preferably about 17 to 20 codons. The oligonucleotides are preferably selected from those oligonucleotides complementary to strategic sites along the pre-mRNA of bcl-2, such as the translation initiation site, donor and splicing sites, or sites for transportation or degradation.

Blocking translation at such strategic sites prevents formation of a functional bcl-2 gene product. It should be appreciated, however, that any combination or subcombination of anticode oligomers, including oligonucleotides complementary or substantially complementary to the bcl-2 pre-mRNA or mRNA that inhibit cell proliferation is suitable for use in the invention. For example, oligodeoxynucleotides complementary to sequence portions of contiguous or non-contiguous stretches of the bcl-2 RNA may inhibit cell proliferation, and would thus be suitable for use in methods of the invention.

Oligonucleotides suitable for downregulating bcl-2 expression also include oligonucleotides complementary or substantially complementary to sequence portions flanking the strategic or other sites along the bcl-2 mRNA. The flanking sequence portions preferably range from about two to about one hundred bases, upstream or downstream of the previously noted sites along the bcl-2 mRNA. These sites preferably range from about five to about twenty codons in length. It is also preferable that the oligonucleotides be complementary to a sequence portion of the pre-mRNA or mRNA that is not commonly found in pre-mRNA or mRNA of other genes, in order to minimize homology of the oligonucleotides for pre-mRNA or mRNA coding strands from other genes.

A number of preferred antisense, or complementary, oligonucleotides for downregulating bcl-2 are listed as follows by Table 3.

TABLE 3

| | | | |
|---|---|---|---|
| translation initiation antisense (TI-AS) | 3' . . . CCCTTCCTACCGCGTGCGAC . . . 5' | | (SEQ ID NO: 6) |
| bcl-2 | 5' . . . CTTTTCCTCTGGGAAGGATGGCGCACGCTGGGAGA . . . 3' | | (SEQ ID NO: 7) |
| splice donor antisense (SD-AS) | 3' . . . CCTCCGACCCATCCACGTAG . . . 5' | | (SEQ ID NO: 8) |
| bcl-2 | 5' . . . ACGGGGTAC . . . GGAGGCTGGGTAGGTGCATCTGGT . . . 3' | (SEQ ID NO: 9) |

TABLE 3-continued

```
splice acceptor    3' . . . GTTGACGTCCTACGGAAACA . . . 5'              (SEQ ID NO: 10)
antisense (SA-AS)

bcl-2              5' . . . CCCCCAACTGCAGGATGCCTTTGTGGAACTGTACGG . . . 3'  (SEQ ID NO: 11)
```

It will be appreciated that antisense oligonucleotides can be employed that comprise more or fewer substituent nucleotides, and/or that extend further along the bcl-2 mRNA chain in either the 3' or 5' direction relative to those listed by Table 3, supra.

Preferably, the antisense oligonucleotide employed in the prodrug of the invention has the same or substantially similar nucleotide sequence as does Genasense (a/k/a oblimersen sodium, produced by Genta Inc., Berkeley Heights, N.J.). Genasense is an 18-mer phosphorothioate antisense oligonucleotide, TCTCCCAGCGTGCGCCAT (SEQ ID NO: 1), that is complementary to the first six codons of the initiating sequence of the human bcl-2 mRNA (human bcl-2 mRNA is art-known, and is described, e.g., as SEQ ID NO: 19 in U.S. Pat. No. 6,414,134, incorporated by reference herein). The U.S. Food and Drug Administration (FDA) has given Genasense Orphan Drug status in August 2000, and has accepted a New Drug Application (NDA) for Genasense in the treatment of cancer. The NDA proposes administering Genasense in combination with dacarbazine for the treatment of patients with advanced melanoma who have not previously received chemotherapy. In addition, the FDA granted Priority Review status to the application, which targets an agency action on or before Jun. 8, 2004. See also, Chi et al., 2001, *Clinical Cancer Research* Vol. 7, 3920-3927, incorporated by reference herein, confirming activity of Genasense in combination therapy of prostate cancer in early clinical trials. The prodrugs of the present invention have the same utility as that recognized for the native (unmodified) 18-mer.

Genasense has been shown to downregulate the production of the Bcl-2 protein and enhance a tumor cell's sensitivity to therapy and ultimately, cause cell death. A number of studies have reported promising results in treatment of several cancers with Genasense in combination with anticancer agents. A phase I/II trial of Genasense in combination with dacarbazine in patients with melanoma has shown promising activity and a Phase III multicenter trial is under way. In addition, Genasense, used in combination with mitoxantrone in patients with hormone-refractory prostate cancer has shown promising results. Kim et al., 2001, Id.

The conjugation of antisense oligonucleotides, such as Genasense, to polymers exemplifies one preferred embodiment of the invention.

In an alternative embodiment, additional suitable antisense oligonucleotides include:

as well as those found in the examples.

B. Formula (I)

In one preferred embodiment of the invention, there are provided oligonucleotide prodrugs of the formula (I):

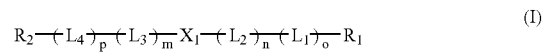

wherein:

$R_1$ and $R_2$ are independently H or a polymer residue;

$L_1$ and $L_4$ are independently selected releasable linking moieties;

$L_2$ and $L_3$ are independently selected spacing groups;

$X_1$ is a nucleotide residue or an oligonucleotide residue; m, n, o and p are independently zero or a positive integer, provided that either (o+n) or (p+m)$\geq$2.

The polymer transport system of the present invention is based in part on the least one of $R_1$ and $R_2$ preferably being a polymeric residue, optionally having a capping group designated herein as A. Suitable capping groups include, for example, OH, $NH_2$, SH, $CO_2H$, $C_{1-6}$ alkyls, as well as oligonucleotide-containing groups such as

and

wherein $X_2$ and $X_3$ are either the same as $X_1$ or another nucleotide or oligonucleotide residue.

The preferred capping groups (II) and (III) allow compositions of formulas (i), (ii), (iii) and (iv) shown below to be formed:

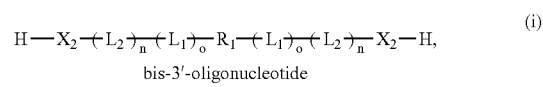

bis-3'-oligonucleotide

```
T-C-T-C-C-A-G-C-G-T-G-C-G-C-C-A-T; (compound 13 - SEQ ID NO: 1)

T-C-T-C-C-A-G-C-A-T-G-T-G-C-C-A-T; (compound 36 - SEQ ID NO: 2)

A-T-C-C-T-A-A-G-C-G-T-G-C-G-C-T-T; (compound 37 - SEQ ID NO: 3)
and
T-C-T-C-C-A-G-X-G-T-G-X-G-C-C-A-T, (compound 38 - SEQ ID NO: 4)
```

-continued

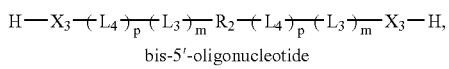
bis-5'-oligonucleotide (ii)

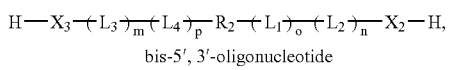
bis-5', 3'-oligonucleotide (iii)

and

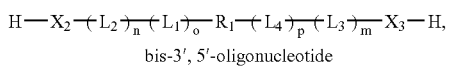
bis-3', 5'-oligonucleotide (iv)

wherein all variables are as previously described.

In another preferred embodiment of the invention, $L_4$ is a releasable linking moiety selected from among the formulas:

wherein:

$Y_{1-25}$ are independently selected from the group consisting of O, S or $NR_9$;

$R_{6-7}$, $R_{9-13}$, $R_{16-25}$, and $R_{27-41}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is a moiety which forms a multi-substituted aromatic hydrocarbon or a multi-substituted heterocyclic group;

$L_{5-12}$ are independently bifunctional spacers;

Z is selected from among moieties actively transported into a target cell, hydrophobic moieties, bifunctional linking moieties and combinations thereof;

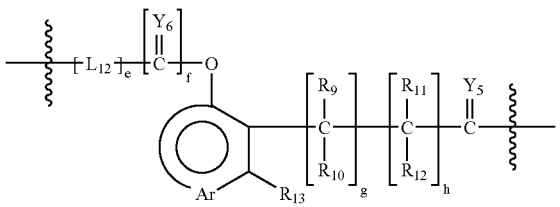

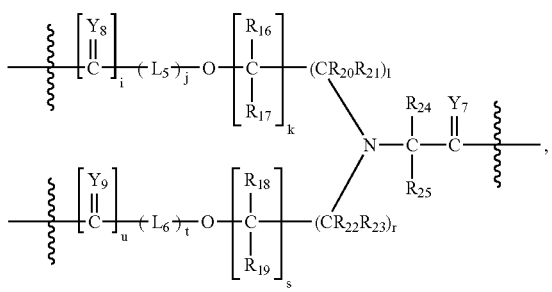

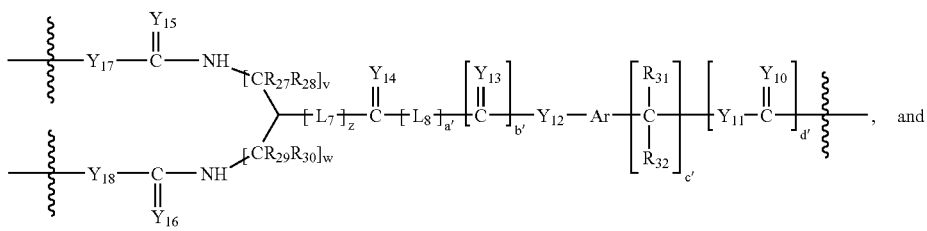
, and

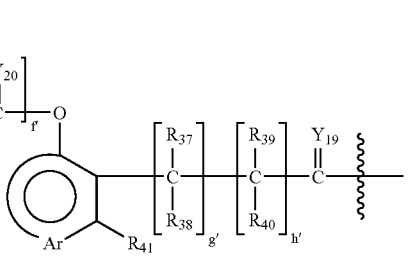

c, h, k, l, r, s, v, w, v', w', c', and h' are independently selected positive integers;

a, e, g, j, t, z, a', z', e' and g' are independently either zero or a positive integer; and b, d, f, i, u, q, b', d' and f' are independently zero or one.

In another preferred embodiment $L_1$ is a releasable linking moiety selected from among the formulas:

—(OCH$_2$CH$_2$)$_s$NH—
—O(CR$_{55}$R$_{56}$)$_s$NH—
—NR$_{59}$(CR$_{57}$R$_{58}$)$_t$C(O)NH(CR$_{55}$R$_{56}$)$_s$C(O)—
—O(CH$_2$)$_s$OC(O)—
—NR$_{59}$(CR$_{55}$R$_{56}$)$_s$C(O)—
—NR$_{59}$(CH$_2$)$_t$(OCH$_2$CH$_2$)$_s$NHC(O)—
—NR$_{59}$(OCH$_2$CH$_2$)$_s$OC(O)—

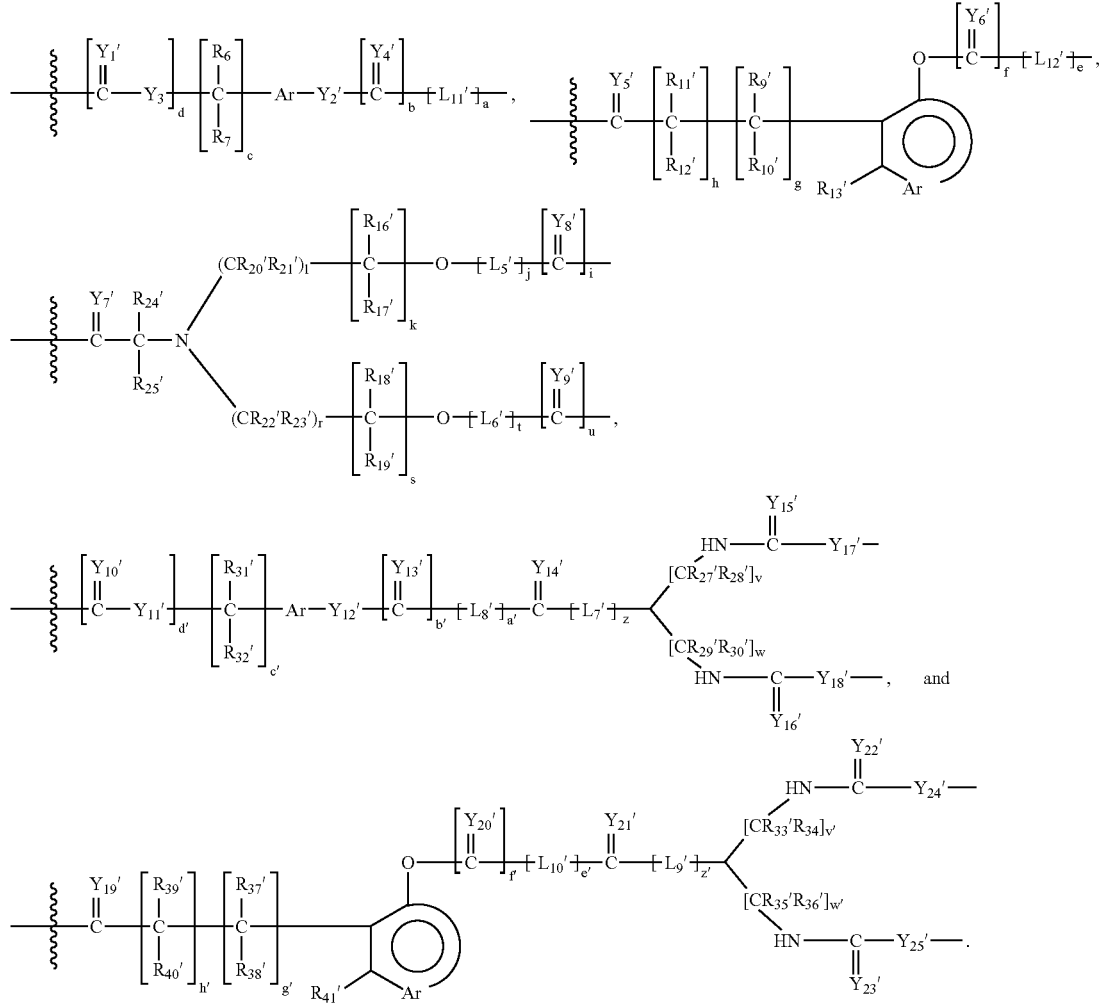

wherein $Y_{1'}$-$Y_{25'}$ are independently selected from the group consisting of O, S or NR$_9$;

$R_{6'-7'}$, $R_{9'-13'}$, $R_{16'-25'}$, and $R_{27'-41'}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and $L_{5'-12'}$ are independently bifunctional spacers.

In some preferred embodiments of the invention, $L_{5-12}$ are independently bifunctional spacers selected from among:
—(CH$_2$)$_3$—,
—C(O)NH(CH$_2$)$_3$—,
—NH(CH$_2$)$_3$—,
—(CR$_{55}$R$_{56}$)$_s$O(CR$_{57}$R$_{58}$)$_t$C(O)—
—NR$_{59}$(CH$_2$)(OCH$_2$CH$_2$)NH—

—O(CR$_{55}$R$_{56}$)$_s$NHC(O)—
—O(CR$_{55}$R$_{56}$)$_s$OC(O)—
(OCH$_2$CH$_2$)$_s$NHC(O)—

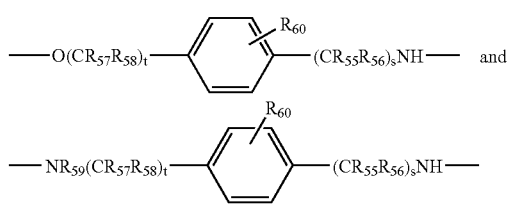

and $L_{5'-12'}$ are independently bifunctional spacers selected from among:
—(CH$_2$)$_3$—, —$(CH_2)_3NH—C(O)$,
—$(CH_2)_3NH—$,
—$C(O)(CR_{57'}R_{58'})_sO(CR_{55'}R_{56'})_{t'}$
—$NH(CH_2CH_2O)_{s'}(CH_2)_rNR_{59'}—$,
—$NH(CH_2CH_2O)_{s'}—$,
—$NH(CR_{55'}R_{56'})_sO—$,
—$C(O)(CR_{55'}R_{56'})_sNHC(O)(CR_{57'}R_{58'})_rNR_{59'}—$,
—$C(O)O(CH_2)_sO—$,
—$C(O)(CR_{55'}R_{56'})_sNR_{59'}—$,
—$C(O)NH(CH_2CH_2O)_{s'}(CH_2)_rNR_{59'}—$,
—$C(O)O—(CH_2CH_2O)_sNR_{59'}—$,
—$C(O)NH(CR_{55'}R_{56'})_sO—$,
—$C(O)O(CR_{55'}R_{56'})_sO—$,
—$C(O)NH(CH_2CH_2O)_{s'}—$,

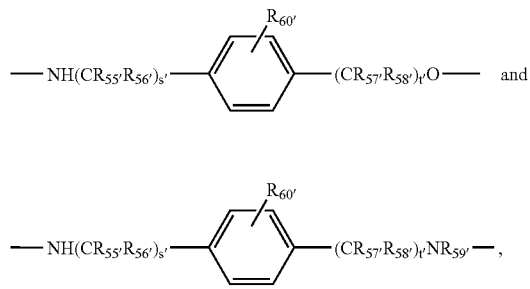

wherein:
$R_{55}$-$R_{59}$ and $R_{55'-59'}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, and $R_{60}$ and $R_{60'}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, $NO_2$, haloalkyl and halogen; and s' and t' are each a positive integer.

In another preferred embodiment of the invention, $L_2$ and $L_3$ are independently spacing groups having about 1 to about 60 carbon atoms and from about 1 to about 10 heteroatoms. Preferably, $L_2$ and $L_3$ are independently spacing groups having from about 2 to about 10 carbon atoms and from about 1 to about 6 heteroatoms. Most preferably, $L_3$ is selected from among:

-$Q(CR_{50}R_{51})_{q'}—$,
-$Q(CR_{50}R_{51})q'O(CR_{52}R_{53})r'$
-$Q(CH_2CH_2O)_{q'}(CR_{52}R_{53})_{r'}—$,
-$QCR_{50}R_{51})_{q'}NHC(O)(CR_{52}R_{53})_{r'}—$,

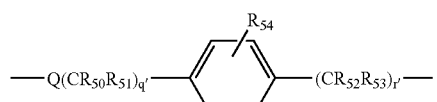

and
-$Q(CH_2)_{q'}—S—S—(CH_2)_{r'}—$; and most preferably, $L_2$ is selected from among:
—$(CR_{50'}R_{51'})_{q'}Q'-$,
—$(CR_{52'}R_{53'})_{r'}O(CR_{50'}R_{51'})_{q'}Q'-$
—$(CR_{52'}R_{53'})_{r'}(OCH_2CH_2)Q'-$,
—$(CR_{52'}R_{53'})_{r'}C(O)NH(CR_{50'}R_{51'})_{q'}Q'-$,

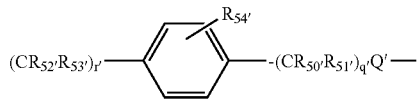

and
—$(CH_2)—S—S—(CH_2)_{q'}Q$- wherein,
Q and Q' are independently selected from O, S or NH;

$R_{50-53}$ and $R_{50'-53'}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{54}$ and $R_{54'}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, $NO_2$, haloalkyl and halogen; and q' and r' are each a positive integer.

With regard to the other variables which comprise the formulae of the present invention, the following are preferred:

$Y_{1-25}$ and $Y_{1'-25'}$ are independently selected from the group consisting of O, S or $NR_9$;

$R_{6-7}$, $R_{9-13}$, $R_{16-25}$, $R_{27-41}$, and $R_{6'-7'}$, $R_{9'-13'}$, $R_{16'-25'}$, and $R_{27'-41'}$ are independently selected from the group consisting of hydrogen, $C_{1-6}$ alkyls, $C_{3-8}$ cycloalkyls, aryls, aralkyls, and $C_{1-6}$ heteroalkyls;

c, h, k, l, r, s, v, w, v', w', c', and h' are one;

a, e, g, j, t, z, a', z', e' and g' are independently either zero or one; and b, d, f, i, u, q, b', d' and f' are independently zero or one.

In yet another preferred embodiment of the invention there are provided compounds of the formula (Ia):

(v)

wherein:
$L_2$ is a spacing group;
$X_1$ is a nucleotide or an oligonucleotide residue;
u' is a positive integer; and
T is a branched polymer which is preferably selected from among those compounds described in commonly assigned PCT publication numbers WO02/065988 and WO02/066066, the disclosure of each being incorporated herein by reference. Within these general formulae, the following are preferred:

23     24
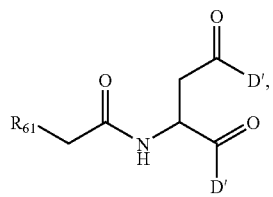
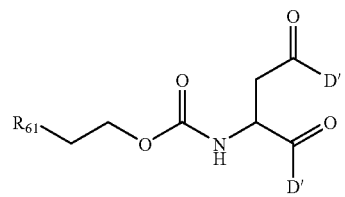
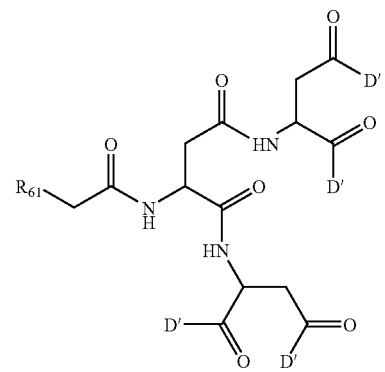
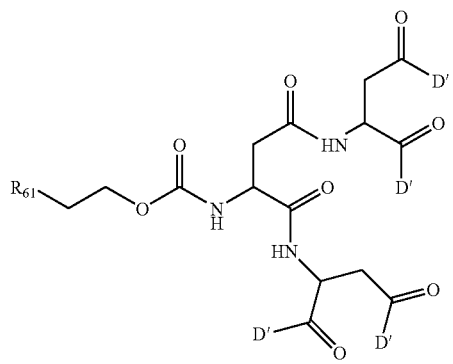
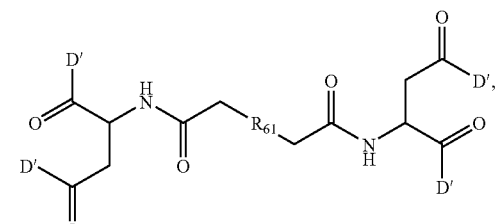
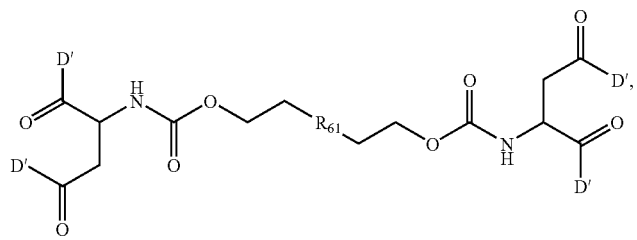
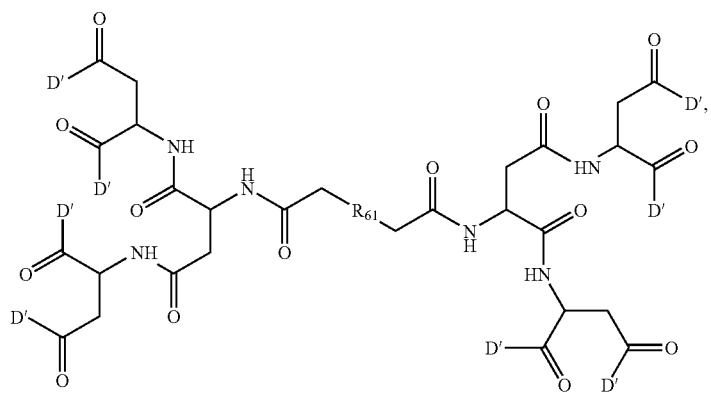

-continued
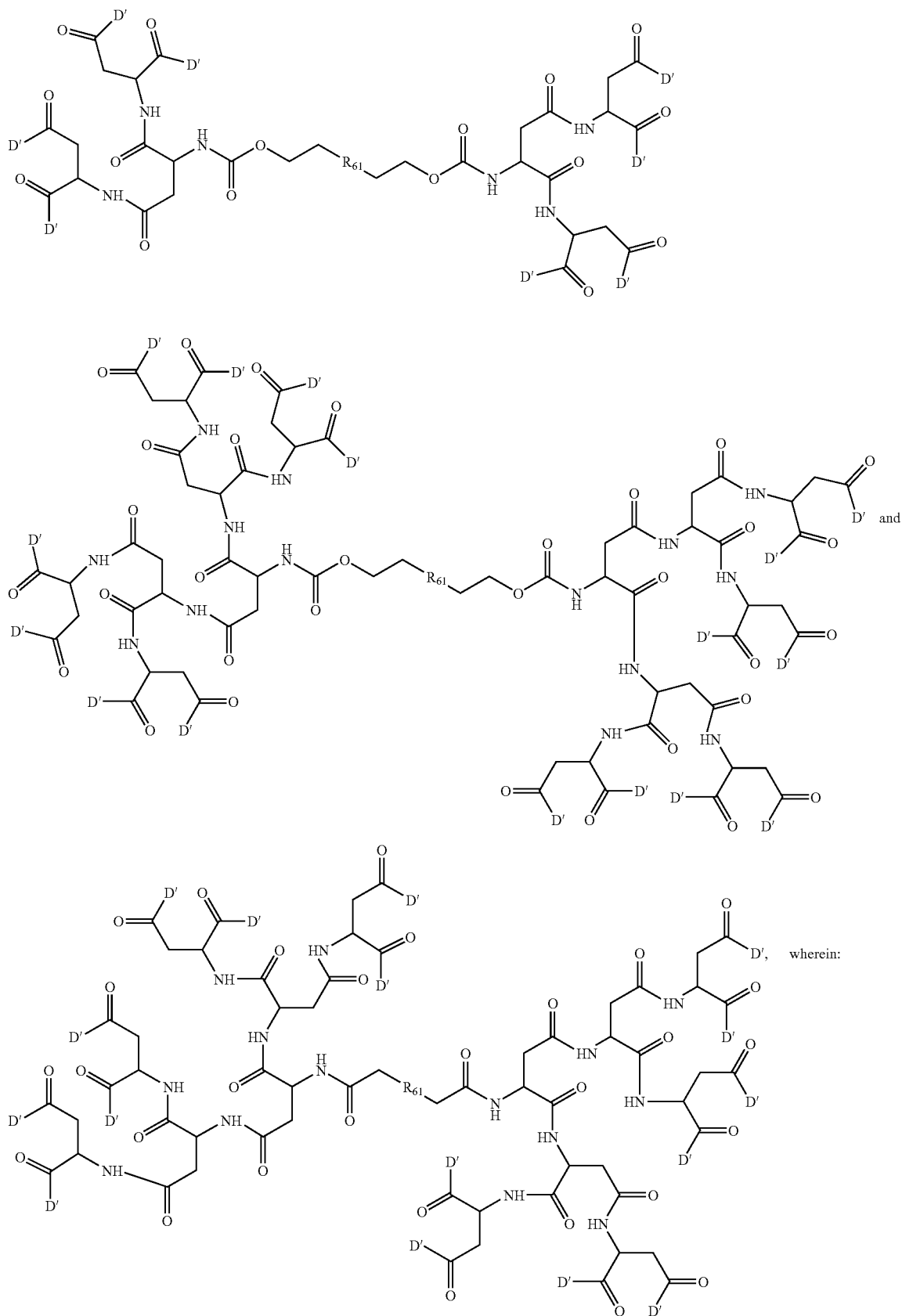
wherein:

D' is one of
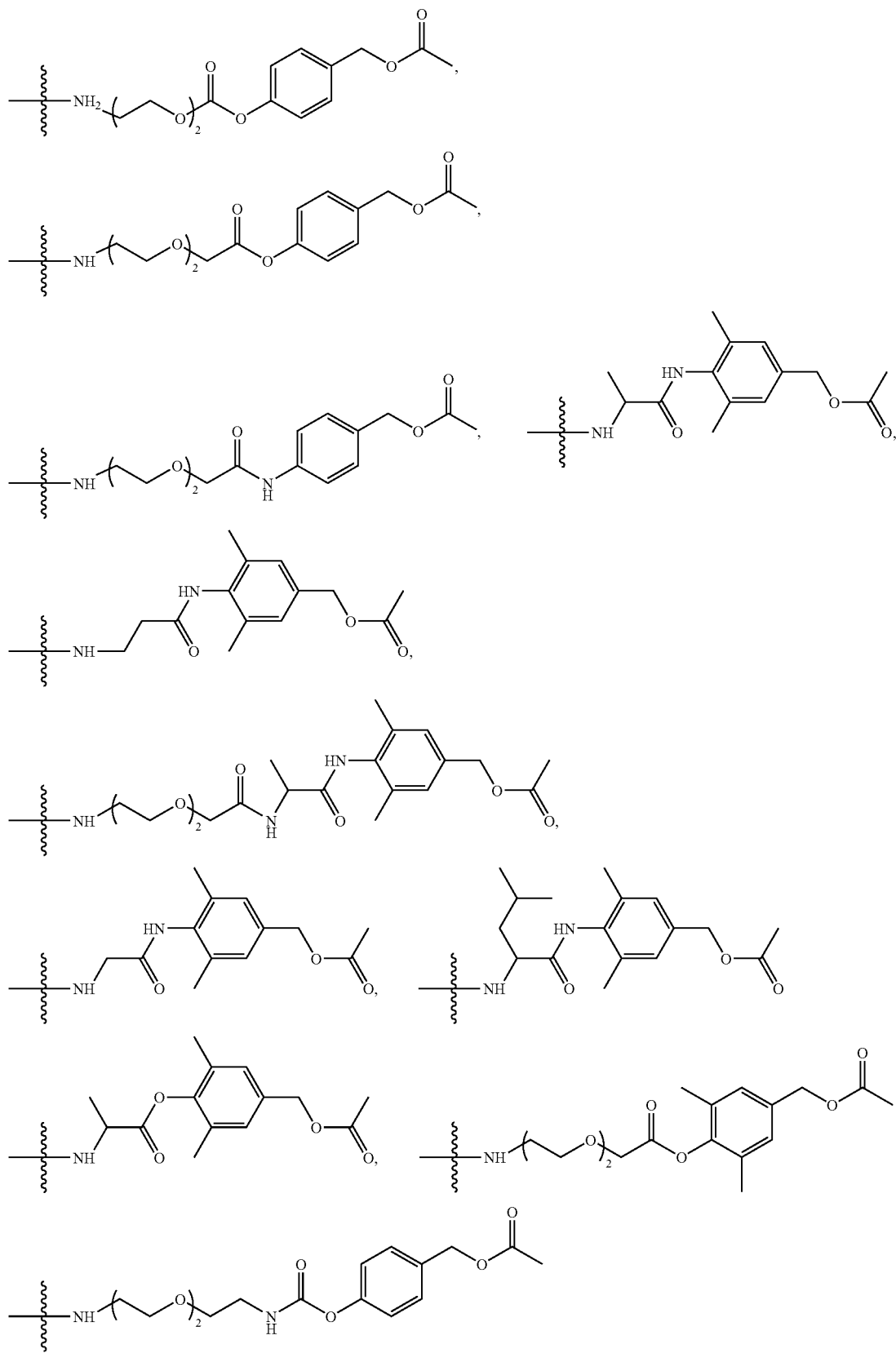

-continued
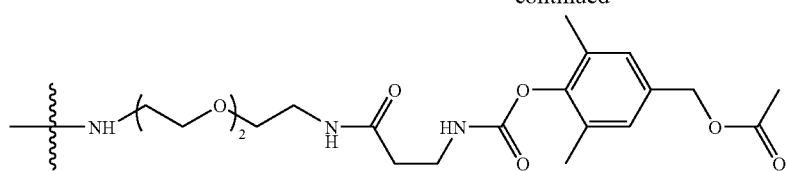
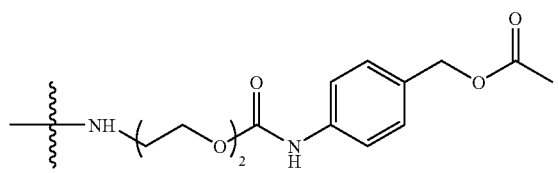
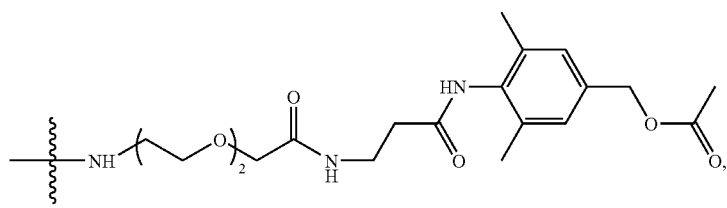
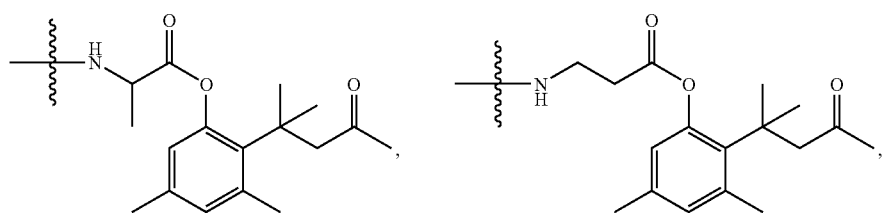
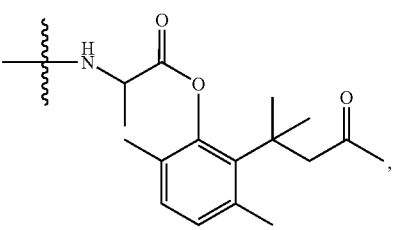
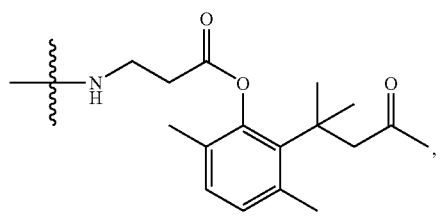
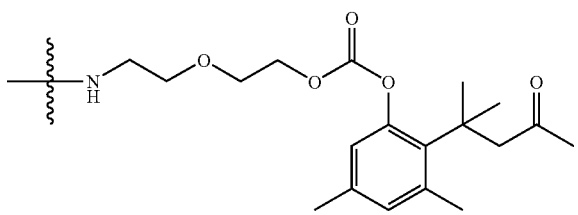
and
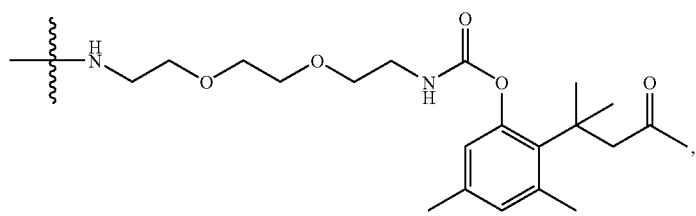

wherein $R_{61}$ is a polymer residue such as that defined for $R_1$ with the understanding that the polymer can be bifunctional when $R_{61}$ is shown with substitutions on both termini; and all other variables are as described above.

For illustrative purposes, a non-limiting compound of formula (Ia) is:

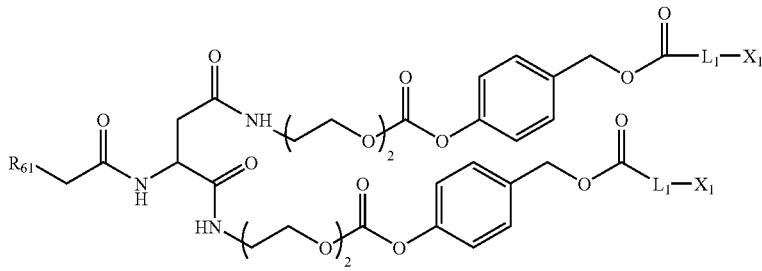

wherein all variables are as described above.

Another aspect of formula (Ia) includes bifunctional compounds that are formed when the polymeric residue ($R_{61}$) includes both an alpha and an omega terminal linking group so that at least four oligonucleotides are delivered. Examples of such polymer conjugates are illustrated below as formulas (vi) and (vii):

wherein all variables are as described above.

In another preferred embodiment of the invention, $L_2$ and $L_3$ are independently spacing groups having about 1 to about 60 carbon atoms and from about 1 to about 10 hetero atoms. Preferably, $L_2$ and $L_3$ are independently spacing groups having from about 2 to about 10 carbon atoms and from about 1 to about 6 heteroatoms. Most preferably, $L_3$ is selected from among:

$-Q(CR_{50}R_{51})_{q'}-$,
$-Q(CR_{50}R_{51})_{q'}O(CR_{52}R_{53})_{r'}-$
$-Q(CH_2CH_2O)_{q'}(CR_{52}R_{53})_{r'}-$,
$-QCR_{50}R_{51})_{q'}NHC(O)(CR_{52}R_{53})_{r'}-$,

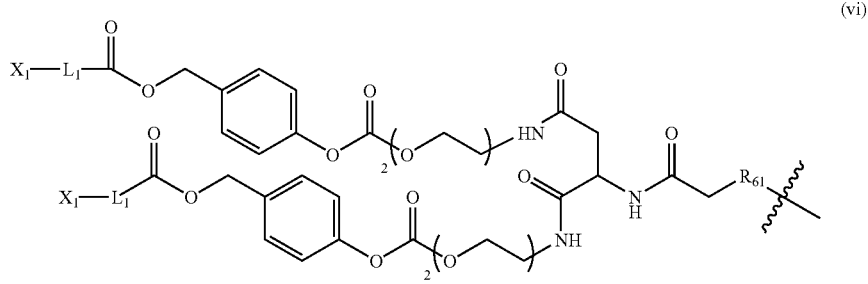

(vi)

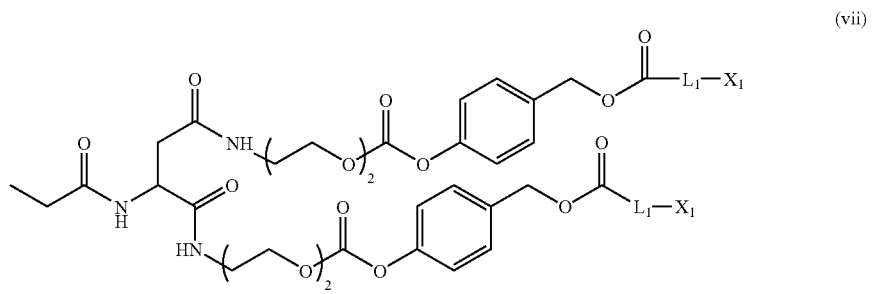

(vii)

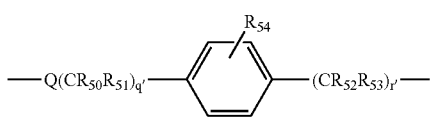

and

—Q(CH$_2$)$_{q'}$—S—S—(CH$_2$)$_{r'}$—, and most preferably, L$_2$ is selected from among:

—(CR$_{50'}$R$_{51'}$)$_{q'}$Q'-,
—(CR$_{52'}$R$_{53'}$)$_{r'}$O(CR$_{50'}$R$_{51'}$)$_{q'}$Q'-,
—(CR$_{52'}$R$_{53'}$)$_{r'}$(OCH$_2$CH$_2$)Q'-,
—(CR$_{52'}$R$_{53'}$)$_{r'}$C(O)NH(CR$_{50'}$R$_{51'}$)$_{q'}$Q'-,

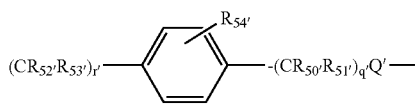

and

—(CH$_2$)—S—S—(CH$_2$)$_{q'}$Q- wherein,

Q and Q' are independently selected from O, S or NH;

R$_{50-53}$ and R$_{50'-53'}$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cyloalkyls, aryls substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy;

R$_{54}$ and R$_{54'}$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cyloalkyls, aryls substituted aryls, aralkyls, C$_{1-6}$ heteroalkyls, substituted C$_{1-6}$ heteroalkyls, C$_{1-6}$ alkoxy, phenoxy, C$_{1-6}$ heteroalkoxy, NO$_2$, haloalkyl and halogen; and q' and r' are each a positive integer.

With regard to the other variables which comprise the formulae of the present invention, the following are preferred:

Y$_{1-25}$ and Y$_{1'-25'}$ are independently selected from the group consisting of O, S or NR$_9$;

R$_{6-7}$, R$_{9-13}$, R$_{16-25}$, R$_{27-41}$, and R$_{6'-7'}$, R$_{9'-13'}$, R$_{16'-25'}$, and R$_{27'-41'}$, are independently selected from the group consisting of hydrogen, C$_{1-6}$ alkyls, C$_{3-8}$ cycloalkyls, aryls, aralkyls, and C$_{1-6}$ heteroalkyls;

c, h, k, l, r, s, v, w, v', w', c', and h' are one;

a, e, g, j, t, z, a', z', e' and g' are independently either zero or one; and b, d, f, i, u, q, b', d' and f' are independently zero or one.

C. Description of the Ar Moiety

In certain aspects of the invention, it can be seen that the Ar moiety is a moiety which when included in Formula (I) forms a multi-substituted aromatic hydrocarbon or a multi-substituted heterocyclic group. A key feature is that the Ar moiety is aromatic in nature. Generally, to be aromatic, the pi electrons must be shared within a "cloud" both above and below the plane of a cyclic molecule. Furthermore, the number of pi electrons must satisfy the Hückel rule (4n+2). Those of ordinary skill will realize that a myriad of moieties will satisfy the aromatic requirement of the moiety for formula (I) and thus are suitable for use herein.

Some particularly preferred aromatic groups include:

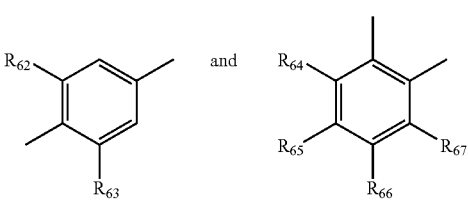

wherein R$_{62-67}$ are independently selected from the same group which defines R$_6$.

Other preferred aromatic hydrocarbon moieties include, without limitation

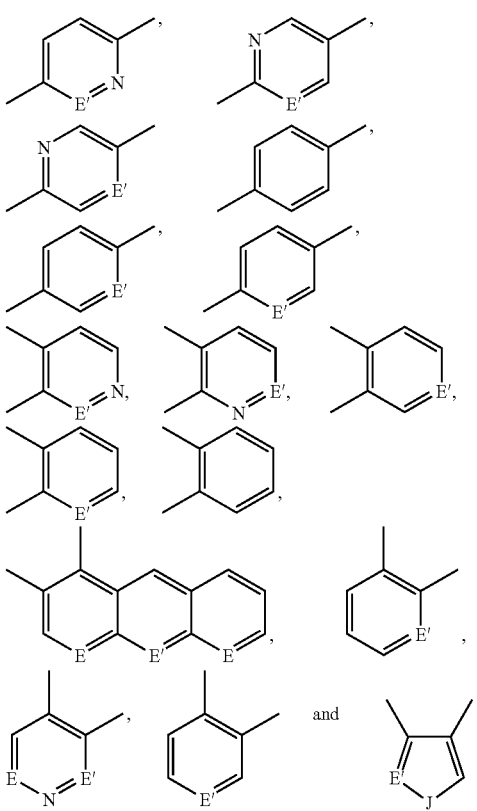

wherein E and E' are independently CR$_{68}$ or NR$_{69}$; and J is O, S or NR$_{70}$ where R$_{68-70}$ are selected from the same group at that which defines R$_6$ or a cyano, nitro, carboxyl, acyl, substituted acyl or carboxyalkyl. Isomers of the five and six-membered rings are also contemplated as well as benzo- and dibenzo-systems and their related congeners are also contemplated. It will also be appreciated by the artisan of ordinary skill that aromatic rings can optionally be substituted with hetero-atoms such as O, S, NR$_9$, etc. so long as Hückel's rule is obeyed. Furthermore, the aromatic or heterocyclic structures may optionally be substituted with halogen(s) and/or side chains as those terms are commonly understood in the art.

D. Polyalkylene Oxides

Referring to Formula (I) it can be seen that R$_1$ and R$_2$ are polymer moieties such as polyalkylene oxide. Suitable examples of such polymers include polyethylene glycols which are substantially non-antigenic. Also useful are polypropylene glycols, such as those described in commonly-assigned U.S. Pat. Nos. 5,643,575, 5,919,455 and 6,113,906. Other PEG's useful in the methods of the invention are described in Shearwater Polymers, Inc. catalog "Polyethylene Glycol and Derivatives 2001". The disclosure of each is incorporated herein by reference. $R_1$ and $R_2$ are preferably PEG derivatives, e.g. —O—$(CH_2CH_2O)_x$— Within this aspect, $R_{1-2}$ are independently selected from among:

J-O—$(CH_2CH_2O)_{n'}$—
J-O—$(CH_2CH_2O)_{n'}$—$CH_2C(O)$—O—,
J-O—$(CH_2CH_2O)_{n'}$—$CH_2CH_2$ $NR_{48}$—,
J-O—$(CH_2CH_2O)_{n'}$—$CH_2CH_2$ SH,
—O—$C(O)CH_2$—O—$(CH_2CH_2O)_{n'}$—$CH_2C(O)$—O—,
—$NR_{48}CH_2CH_2$—O—$(CH_2CH_2O)_{n'}$—$CH_2CH_2$ $NR_{48}$—,
—$SHCH_2CH_2$—O—$(CH_2CH_2O)_{n'}$—$CH_2CH_2$ SH—, wherein n' is the degree of polymerization selected so that the weight average molecular weight is at least about 2,000 Da to about 136,000 Da;

$R_{48}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and J is a capping group such as methyl or a complementary linking group which allows a bifunctional polymer to be provided.

Although PAO's and PEG's can vary substantially in weight average molecular weight, preferably, $R_1$ and $R_2$ independently have a weight average molecular weight of from about 2,000 Da to about 136,000 Da in most aspects of the invention. More preferably, $R_1$ and $R_2$ independently have a weight average molecular weight of from about 3,000 Da to about 100,000 Da, with a weight average molecular weight of from about 5,000 Da to about 40,000 Da being most preferred.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

E Synthesis of Oligonucleotide Polymer Conjugates

Generally the prodrugs are prepared by a) reacting a compound of the formula:

$R_2$-$L_4$-leaving group with a compound of the formula:

H-$L_3$-$X_1$ under conditions sufficient to form a prodrug of the formula $R_2$-$L_4$-$L_3$-$X_1$, wherein:

$R_2$ is a polymer residue;
$L_4$ is a releasable linking moiety;
$L_3$ is a spacing group;
$X_1$ is a nucleotide or an oligonucleotide residue.

Within this aspect of the invention, it is preferred to employ activated polymers which already contain the releasable linkers attached thereto. A non-limiting list of suitable combinations include the releasable PEG-based transport systems described in commonly-assigned U.S. Pat. Nos. 6,624,142, 6,303,569, 5,965,119, 6,566,506, 5,965,119, 6,303,569, 6,624,142, and 6,180,095, the contents of each are incorporated herein by reference.

Specific examples include but are not limited to,

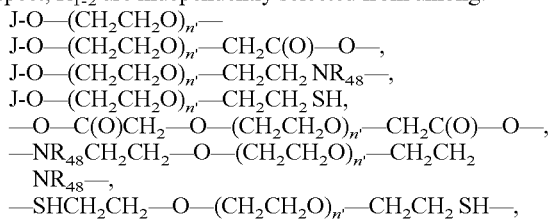

(PEG mw 12,000)

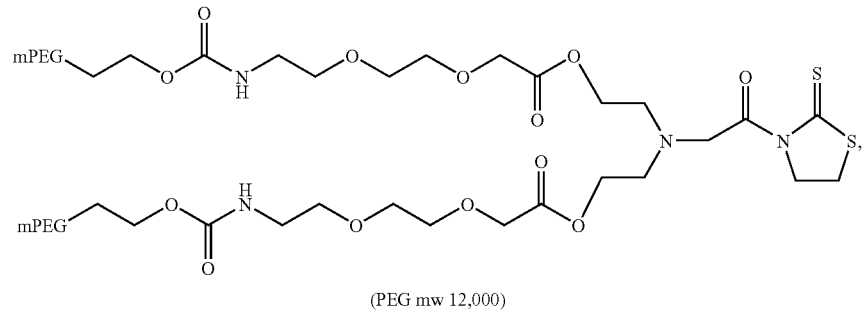

(PEG mw 12,000)

it being understood of course that the molecular weight of the polymer portion can be varied according to the needs of the artisan.

The polymer releasable linker shown above is then reacted with a modified oligomer under conditions sufficient to allow the conjugate to be formed.

Any of the nucleotides or oligonucleotides described above can be functionalized on one of the 5'- or 3'-terminal phosphate or phosphorothioate using routine techniques such as the phosphoramidite methods to attach a desired alkyl-amino or other group onto the terminal phosphate. For example, a blocked (Fmoc) amino alkyl is attached, the resultant compound is oxidized, deprotected and purified.

Synthesis of specific oligonucleotide polymer conjugates or prodrugs is set forth in the Examples. Alternatively, the prodrugs can be prepared by:
1) reacting an activated PEG polymer with a protected bifunctional releasable linking group under suitable coupling conditions to form a first intermediate,
2) deprotecting and activating the intermediate of step 1) with a suitable activating group such as NHS ester, and
3) reacting the activated intermediate of step 2) with a modified oligonucleotide in a PBS buffered system to obtain the desired oligonucleotide polymer prodrug.

A non-limiting list of activated polymers include bis-succinimidyl carbonate activated PEG (SC-PEG), bis-thiazolidine-2-thione activated PEG (T-PEG), N-hydroxyphthalamidyl carbonate activated PEG (BSC-PEG),(see commonly assigned U.S. Ser. No. 09/823,296, the disclosure of which is incorporated herein by reference), succinimidyl succinate activated PEG (SS-PEG) and mono-activated PEG's such as those found in, for example, in the aforementioned 2001 Shearwater Catalog.

Conjugation of the activated PEG polymer to the protected bifunctional releasable linking group can be carried out in the presence of a coupling agent. A non-limiting list of suitable coupling agents include 1,3-diisopropylcarbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as tetrahydrofuran (THF), acetonitrile ($CH_3CN$), methylene chloride (DCM), chloroform ($CHCl_3$), dimethyl formamide (DMF) or mixtures thereof, and at a temperature from 0° C. up to about 22° C. (room temperature).

Conjugation of the modified oligonucleotide to the PEG-releasable linker can be carried out in a PBS buffered system in the pH range of about 7.4-8.5. The artisan of course will appreciate that synthesis of the prodrugs described herein, will also include the use of commonly found laboratory conditions, i.e. solvents, temperature, coupling agents etc. such as those described in the examples.

Regardless of the synthesis selected, some of the preferred compounds which result from the synthetic techniques described herein include:

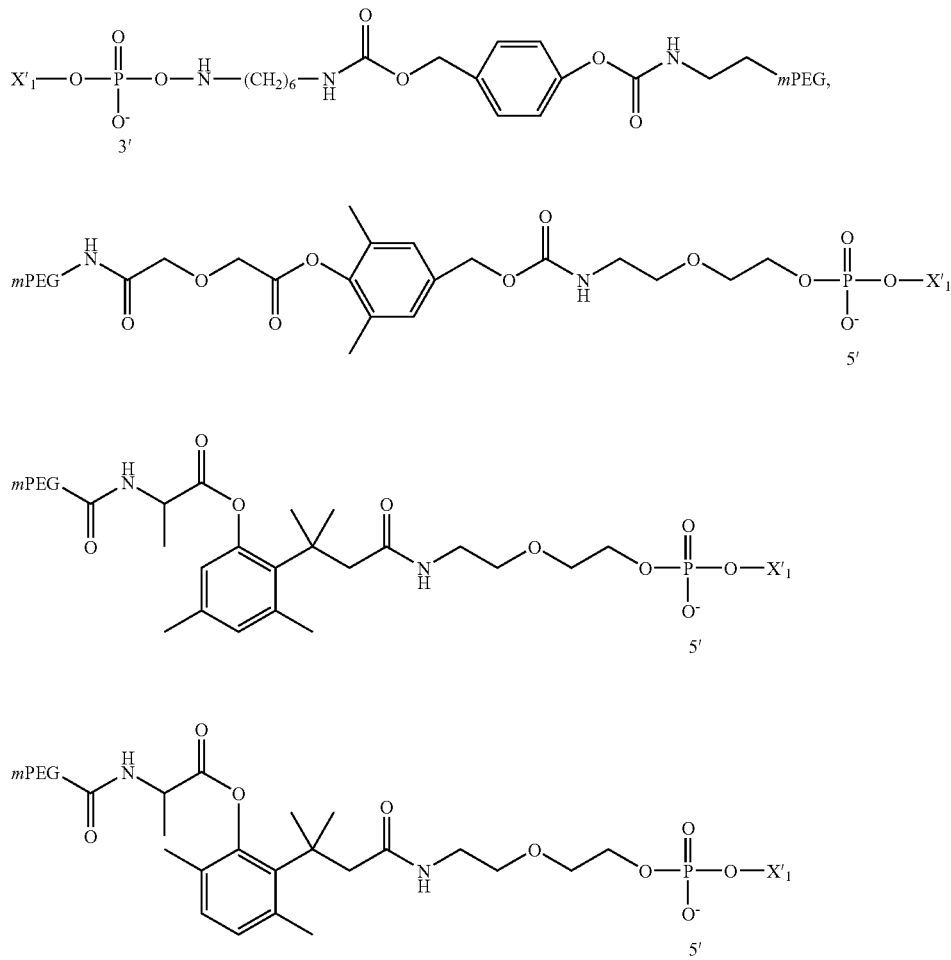

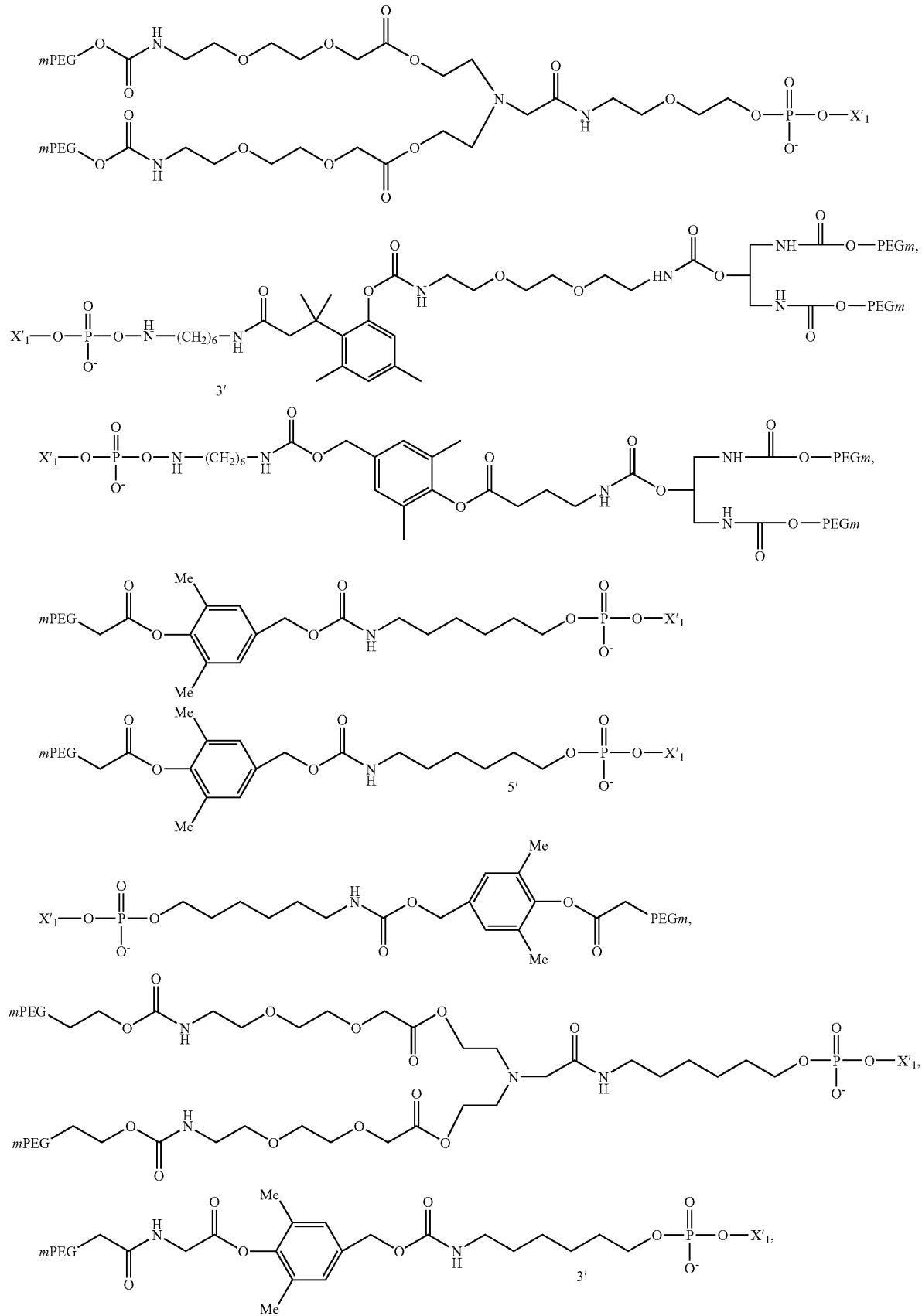

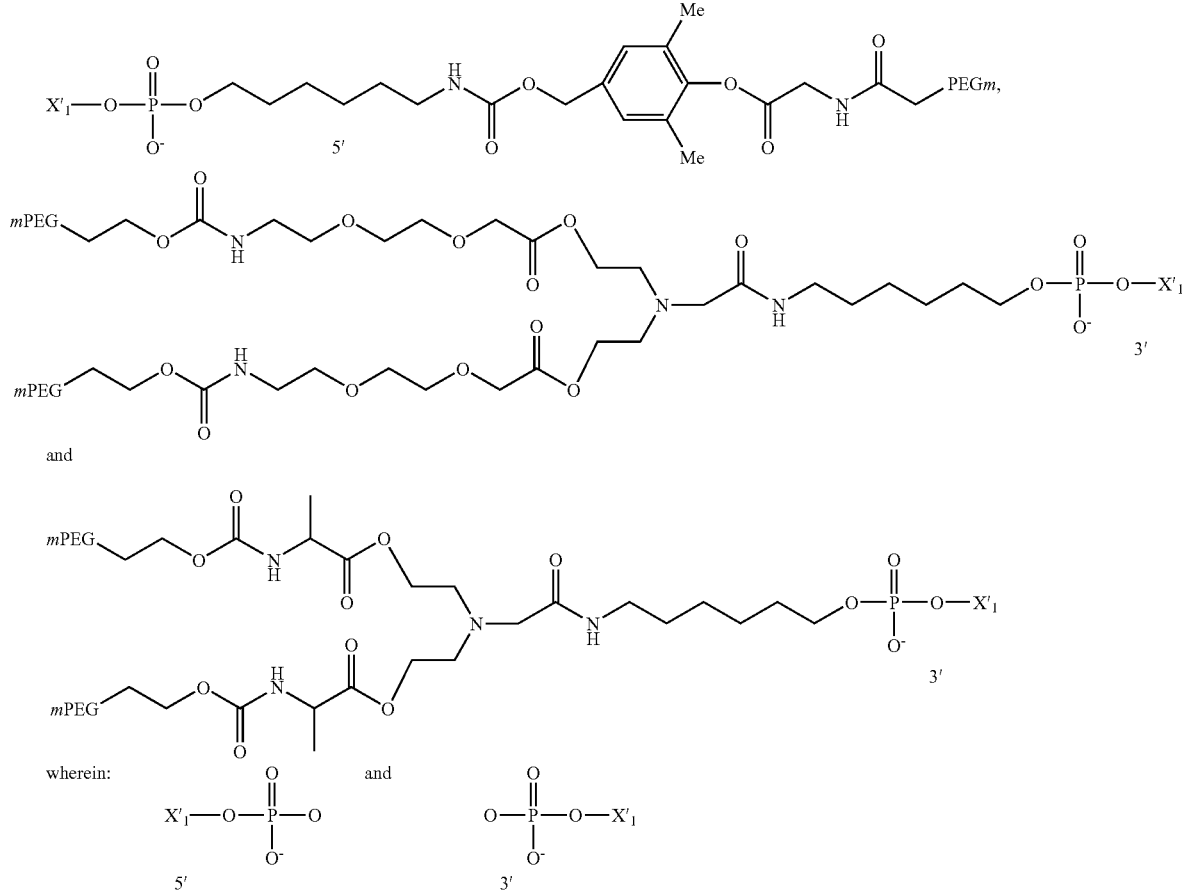
represent an oligonucleotide and point of terminal phosphate modification and mPEG is $CH_3-O-(CH_2-CH_2-O)_x-$; wherein x is a positive integer selected from about 10 to about 2300.
More preferred compounds of the invention include:
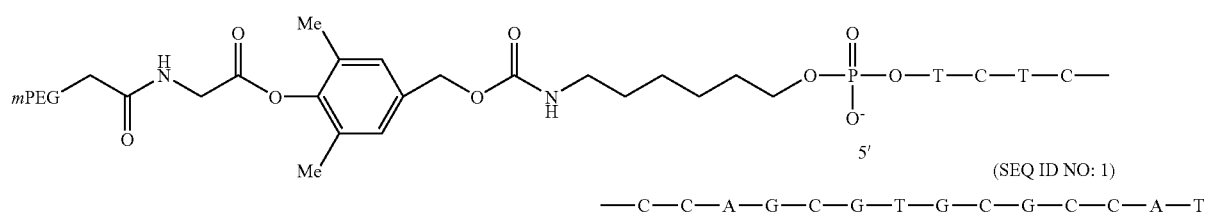
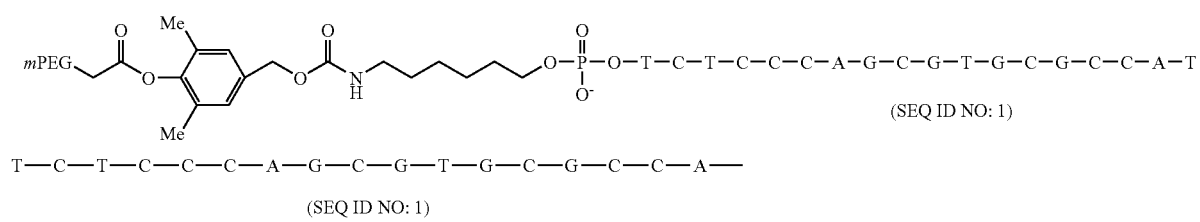

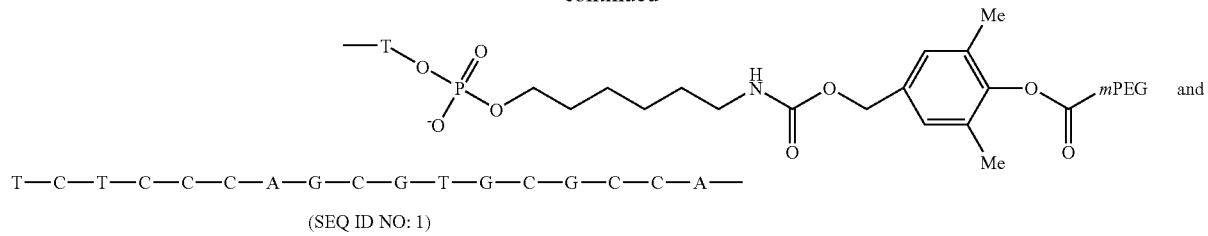

T—C—T—C—C—C—A—G—C—G—T—G—C—G—C—C—A—

(SEQ ID NO: 1)

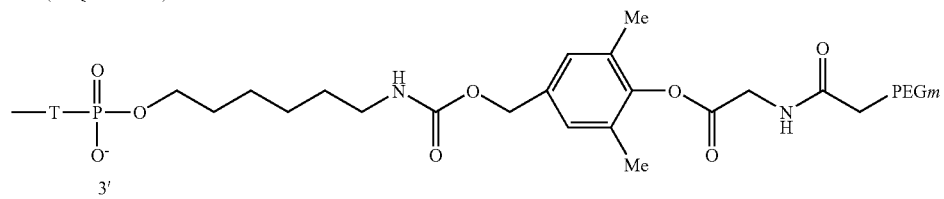

G. Methods of Treatment

Another aspect of the present invention provides methods of treatment for various medical conditions in mammals. The methods include administering to the mammal in need of such treatment, an effective amount of an oligonucleotide prodrug, which has been prepared as described herein. The compositions are useful for, among other things, treating neoplastic disease, reducing tumor burden, preventing metastasis of neoplasms and preventing recurrences of tumor/neoplastic growths, liver diseases, viral diseases such as, HIV, in mammals. The prodrugs of the present invention can be used for whatever indication the native olignucleotide or antisense oligonucleotides are used for, i.e. cancer therapy, etc. Simply by way of example, the inventive prodrugs are contemplated to be employed in the treatment of multiple myeloma, chronic lymphocytic leukemia, non-small cell lung cancer, small cell lung cancer, prostate cancer and other tumors or cancers too numerous to mention.

The amount of the prodrug administered will depend upon the parent molecule included therein an condition being treated. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

It is also contemplated that the prodrugs of the invention be administered in combination (e.g., simultaneously and/or sequentially) with other art-known anticancer agents. Suitable anticancer agents include, simply by way of example: (Paclitaxel; Bristol Myers Squibb); Camptosar® (Irinotecan; Pfizer.); Gleevec® (Imatiinib Mesylate; Novartis); Rituxan® (Rituximab; Genentech/IDEC); Fludara® (Fludarabine; Berlex Labs); Cytoxan® (cyclophosphamide; Bristol Myers Squibb); Taxotere® (Docetaxel; Aventis Pharmaceuticals); Mylotarg® (Gemtuzumab ozogamicin; Wyeth-Ayerst); Cytosine arabinoside and/or dexamethasone, to name but a few such agents.

EXAMPLES

The following examples serve to provide further appreciation of the invention but are not meant in any way to restrict the effective scope of the invention. The underlined and bold-faced numbers recited in the Examples correspond to those shown in the Figures. In each of the figures, the sugar moiety and phosphate backbone are represented as:

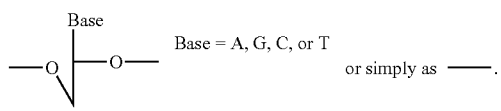

The MPEG designation shall be understood to represent

General Procedures. All the conjugation reactions between PEG linkers and oligonucleotides were carried out in PBS buffer systems at room temperature. Extraction with organic solvents in general removed the un-reacted oligonucleotides, further anion-exchange chromatography separated PEG-Oligo conjugates from non-reacted excess PEG linkers to give pure products.

HPLC methods. The reaction mixtures and the purity of intermediates and final products were monitored by a Beckman Coulter System Gold® HPLC instrument employing a ZORBAX® 300 SB C-8 reversed phase column (150×4.6 mm) or a Phenomenex Jupiter® 300A C18 reversed phase column (150×4.6 mm) with a multiwavelength UV detector, using a gradient of 30-90% of acetonitrile in 0.5% trifluoroacetic acid (TFA) and 25-35% acetonitrile in 50 mM TEAA buffer with 4 mM TBACl at a flow rate of 1 mL/min. The anion exchange chromatography was run on Bio-Cad 700E Perfusion Chromatography Workstation from Applied Biosystems using either Poros 50HQ strong anion exchange resin from Applied Biosystems or DEAE Sepharose fast flow weak anion exchange resin from Amersham Biosciences packed in an AP-Empty glass column from Waters. Desalting was achieved by using HiPrep 26/10 or PD-10 desalting columns from Amersham Biosciences.

Example 1

Compound 3. A solution of compound 1 (440 mg, 0.036 mmol) and 2 (5 mg, 3.6 µmol) in PBS buffer (10 mL, pH 7.4) was stirred at room temperature for 12 hrs. The reaction solution was extracted with methylene chloride (DCM, 3×10 mL) and the combined organic layers were dried ($MgSO_4$), filtered, and the solvent evaporated under reduced pressure. The residue was dissolved in double distilled water (1.5 mL per 100 mg) and loaded on a HQ/10 Poros strong anion exchange column (10 mm×60 mm, bed volume ~6 mL). The un-reacted PEG linkers were eluted with water (3~4 column volumes) and the product then eluted with 0.2 M $NH_4HCO_3$ solution (~2 column volumes). The fractions containing pure product were pooled and lyophilized to yield pure 3 (19 mg, 1.44 mmol, 40%).

Examples 2-6

Compounds 5, 7, 9, 11, and 12 were made and purified in the similar way as 3 in the yields ranging from 30% to 50%.

Example 7

Compound 14. To a solution of compound 13 (10 mg, 1.7 µmol) in PBS buffer (5 mL, pH 7.4) was added 10 (175 mg, 85 µmol) in five equivalent portions every hour and stirred at room temperature for 12 hrs. The reaction solution was extracted with DCM (3×10 mL) and brine (10 mL), and the combined organic layers were dried ($MgSO_4$), filtered, and the solvent evaporated under reduced pressure. The residue was dissolved in double distilled water (1.5 mL) and loaded on a DEAE fast flow, weak anion exchange column (10 mm×60 mm, bed volume ~6 mL) which was pre-equilibrated with 20 mM tris-HCl buffer, pH 7.4. The unreacted PEG linkers were eluted with water (3 to 4 column volumes) and the product then eluted with a gradient of 0 to 100% 1 M NaCl in 20 mM Tris-HCl buffer 7.4 in 10 min, followed by 100% 1M NaCl for 10 min at a flow rate of 3 mL/min. The fractions containing pure product were pooled and desalted on a PD-10 desalting column with 0.2 M $NH_4HCO_3$ solution (~2 column volumes) and the resulting solution was lyophilized to yield pure 14 (25 mg, 0.95 µmol, 57%).

Example 8

Compound 16 was made and purified the same way as 14, with a 60% yield.

Example 9

Compound 17. To a solution of AS1 (5 mg, 0.85 µmol) in phosphate buffer (2 mL, pH 7.8) was added 10 (175 mg, 0.085 mmol) which was divided into five equivalent portions in 2 hrs and the resulting solution stirred at room temperature for another 2 hrs. The reaction solution was extracted with DCM (3×6 mL) and brine (5 mL), and the combined organic layers were dried ($MgSO_4$), filtered, and the solvent evaporated under reduced pressure. The residue was dissolved in double distilled water (5 mL) and loaded on a DEAE fast flow, weak anion exchange column (10 mm×60 mm, bed volume ~6 mL) which was pre-equilibrated with 20 mM tris-HCl buffer, pH 7.4. The unreacted PEG linkers were eluted with water (3 to 4 column volumes) and the product then eluted with a gradient of 0 to 100% of 1 M NaCl in 20 mM Tris-HCl buffer, pH 7.4, for 10 minutes followed by 100% 1M NaCl at a flow rate of 3 mL/min for 10 minutes. The fractions containing pure product were pooled and desalted on a PD-10 desalting column and the resulting solution was lyophilized to yield pure 17 (15 mg, 0.57 µmol, 67%).

Examples 10-11

Compounds 18 and 19 were made and purified the same way as 17 with yields of 67% for the final products using AS2 and AS3 in place of AS1.

Examples 12-15

Compound 21 was made and purified the same way as 14 by replacing 12 with 20 with a yield of 90%.

Compound 22 was made and purified in the same way as 14 by replacing 12 with 20 with a yield of 65%.

Compound 24 was made and purified in the same way as 14 by replacing 12 with 23 and, for desalting, water (~2 column volumes) was used to elute the product instead of 0.2 M $NH_4HCO_3$ solution. The final was 30%.

Compound 26 was made and purified in the same way as 24 by replacing 23 with 25. The yield was 30%.

Example 16

Compound 27. To a solution of 13 (10 mg, 1.7 µmol) in phosphate buffer (5 mL, pH 8.5) was added 27 (180 mg, 0.084 mmol) which was divided into ten equivalent portions, and the resulting solution stirred at room temperature for 4 days. The reaction solution was extracted with DCM (3×10 mL) and brine (10 mL), and the combined organic layers were dried ($MgSO_4$), filtered, and the solvent evaporated under reduced pressure. The residue was dissolved in double distilled water (1.5 mL) and loaded on a DEAE fast flow, weak anion exchange column (10 mm×60 mm, bed volume ~6 mL) which was pre-equilibrated with 20 mM tris-HCl buffer, pH 7.4. The un-reacted PEG linkers were eluted with water (3 to 4 column volumes) and the product then eluted with a gradient of 0 to 100% 1 M NaCl in 20 mM Tris-HCl buffer, pH 7.4, for 10 min, followed by 100% 1M NaCl at a flow rate of 3 mL/min for 10 minutes. The fractions containing pure product were pooled and desalted on a PD-10 desalting column and the resulting solution was lyophilized to yield 14 (105 mg, 0.0102 mmol, 60%). The purity of the product was determined by HPLC.

Examples 17-21

Compounds 29, 30 and 31 were made and purified the same way as 28, except that 13 was replaced by AS1, AS2 and AS3, respectively. A yield of 65% was obtained for each of the final products.

Compound 33 was made and purified the same way as 14 with 32 replacing 12 resulting in a yield of 76%.

Compound 35 was made and purified the same way as 14 except that activated PEG 34 was used in place of 10. The final yield was 30%.

Biological Data

Some in vitro properties of PEG-Oligo conjugates are summarized below:

TABLE 4

In vitro properties of PEG-Oligo conjugates

| Compound | $t_{1/2}$ (buffer) | $t_{1/2}$ (Rat Plasma) | $t_{1/2}$ (PE I) | $t_{1/2}$ (PE II) | $t_{1/2}$ (NucleaseP1) |
|---|---|---|---|---|---|
| 3  | >>24 h | 0.7 h  | <5 min | >24 h | <5 min |
| 7  | >>24 h | 0.5 h  | <5 min | >24 h | <5 min |
| 5  | >>24 h | 0.5 h  | <5 min | >24 h | <5 min |
| 9  | >>24 h | 3.7 h  | <5 min | 36    | 0.3 h  |
| 11 | >>24 h | 2.3 h  | <5 min | 63    | 0.3 h  |
| 12 | >>24 h | 10.6 h | <5 min | 1.7   | <5 min |
| 14 | >>24 h | 14.7 h | <5 min | 38.9  | 0.3 h  |
| 16 | >>24 h | 13.8 h | <5 min | 42.7  | 0.3 h  |
| 21 | >>24 h | 6.5 h  | >24 h  | >24 h | <5 min |

TABLE 4-continued

In vitro properties of PEG-Oligo conjugates

| Compound | $t_{1/2}$ (buffer) | $t_{1/2}$ (Rat Plasma) | $t_{1/2}$ (PE I) | $t_{1/2}$ (PE II) | $t_{1/2}$ (NucleaseP1) |
|---|---|---|---|---|---|
| 24 | >>24 h | 11. h  | 18.7 h | 36.8 h | <5 min |
| 28 | >>24 h | >48 h  | >24 h  | >48 h  | <5 min |
| 33 | >>24 h | >48 h  | >24 h  | >48 h  | <5 min |
| 35 | >>24 h | 4.1 h  | 5.6 h  | >48 h  | <5 min |

PE I = Phosphodiesterase I, 5'-exonuclease, kinetics done in pH 8.8 TEAA buffer at 37° C.;
PE II = Phosphodiesterase II, 3'-exonuclease, kinetics done in pH 6.5 TEAA buffer at 37° C.;
NucleaseP1 = endonuclease, kinetics done in pH 5.3 TEAA buffer at 37° C.;
for all enzymes 1 unit releases 1 µmol of oligonucleotide.

Pharmacokinetics of PEG-Oligo Conjugate in ICR Mice

General Procedures.

1) Animal Husbandry: Mice were housed 6 per cage, in breeder boxes. Cages were sized in accordance with the "Guide for the Care and Use of Laboratory Animals of the Institute of Laboratory Animal Resource", National Research Council.

2) Diet: The mice had access to tap water and were fed commercially available lab chow ad libitum.

3) Compound Preparation: Compound 13 was dissolved in 4.0 mL of saline and compound 14 was dissolved in 4.1 mL of saline.

4) Administration Site: Compound 13 and 14 were administered as a single dose (Day 1) via the tail vein.

Experimental Design

Sixty (60) mice were assigned, dosed and bled according to the following design, shown by Table 5, below.

TABLE 5

| Grp | Tx | N | Dose (mg/kg) | Dose* (mg/kg) | Inj | Time Points Bled (h) | | | | | | | | | Vol (µl) |
|---|---|---|---|---|---|---|---|---|---|---|---|---|---|---|---|
| 1  | 14 | 3 | 120 | 4 | iv | 0.03 | | | | | | | | | 1000 |
| 2  | 14 | 3 | 120 | 4 | iv | | 0.25 | | | | | | | | 1000 |
| 3  | 14 | 3 | 120 | 4 | iv | | | 0.5 | | | | | | | 1000 |
| 4  | 14 | 3 | 120 | 4 | iv | | | | 1 | | | | | | 1000 |
| 5  | 14 | 3 | 120 | 4 | iv | | | | | 3 | | | | | 1000 |
| 6  | 14 | 3 | 120 | 4 | iv | | | | | | 6 | | | | 1000 |
| 7  | 14 | 3 | 120 | 4 | iv | | | | | | | 24 | | | 1000 |
| 8  | 14 | 3 | 120 | 4 | iv | | | | | | | | 48 | | 1000 |
| 9  | 14 | 3 | 120 | 4 | iv | | | | | | | | | 72 | 1000 |
| 10 | 14 | 3 | 120 | 4 | iv | | | | | | | | | | 96 | 1000 |
| 11 | 13 | 3 | 4   | 4 | iv | 0.03 | | | | | | | | | 1000 |
| 12 | 13 | 3 | 4   | 4 | iv | | 0.25 | | | | | | | | 1000 |
| 13 | 13 | 3 | 4   | 4 | iv | | | 0.5 | | | | | | | 1000 |
| 14 | 13 | 3 | 4   | 4 | iv | | | | 1 | | | | | | 1000 |
| 15 | 13 | 3 | 4   | 4 | iv | | | | | 3 | | | | | 1000 |
| 16 | 13 | 3 | 4   | 4 | iv | | | | | | 6 | | | | 1000 |
| 17 | 13 | 3 | 4   | 4 | iv | | | | | | | 24 | | | 1000 |
| 18 | 13 | 3 | 4   | 4 | iv | | | | | | | | 48 | | 1000 |
| 19 | 13 | 3 | 4   | 4 | iv | | | | | | | | | 72 | 1000 |
| 20 | 13 | 3 | 4   | 4 | iv | | | | | | | | | | 96 | 1000 |

*oligo equivalent

Three (3) untreated mice were bled via cardiac puncture into EDTA containing tubes for the collection of untreated control plasma.

The mice were injected intravenously with 100 μL per mouse with native compound 13 and 14. Following sedation with 0.09% Avertin, the mice were terminally bled ~1000 μL by cardiac puncture. Blood was collected into EDTA containing vials. The plasma was collected following centrifugation of the blood and immediately frozen at −80° C. on dry ice.

Clinical Examinations:

The mice were examined visually once daily following infusion of the test article, for mortality and signs of reaction to treatment. Any death and clinical signs was recorded. Body weights were measured prior on the day of injection only.

The pharmacokinetic studies for compounds 28 and 33 were done in a similar fashion.

Experimental Results

The pharmacokinetic results are summarized in the following Table 6, below.

TABLE 6

In vivo properties of PEG-Oligo conjugates

| Compound | Cmax (μg/mL) | Plasma Half-life (hr) | AUC (hr · μg/mL) |
| --- | --- | --- | --- |
| 13 | 14.9 | 0.19 | 4.1 |
| 14 | 54.8 | 0.66 | 51.8 |
| 28 | 491.2 | 1.05 | 730.6 |
| 33 | 556.7 | 0.25 | 191.0 |

Examples 22-25

Confirmation of In Vitro Activity of Antisense PEG Conjugates

Bcl-2 protein has been shown to have significant anti-apoptotic activity in prostate cancer cells. Downregulation of bcl-2 protein in prostate cancer cells is confirmed by cell death, and induction of cell death by bcl-2 antisense PEG conjugates was employed to confirm the successful intracellular delivery of the antisense oligonucleotides.

Materials And Methods For Examples 22-25

The tested compounds are listed by Table 6, below.

TABLE 7

| Compound | Description |
| --- | --- |
| 14 | 5' G aromatic releasable |
| 28 | 5'- permanent |
| 33 | 5' G-->A aromatic releasable |
| 24 | 24k-mPEG-BCN3-5' aliphatic releasable |
| 35 | 20k-mPEG-RNL9 5' releasable (intermediate $t_{1/2}$ in rats) |

These were prepared as described supra.

Cell Culture

Mycoplasma-free PC3 cells were obtained from the American Type Culture Collection (Rockville, Md.) were grown in Roswell Park Memorial Institute media ("RPMI") (Invitrogen, Grand Island, N.Y.) plus 10% fetal bovine serum ("FBS"), containing 10% (v/v) heat inactivated (56° C.) FBS supplemented with 1% non-essential amino acids, 1% pyruvate, 25 mM HEPES (N-2-Hydroxyehtylpiperazine-N'-2-ethanesulfonic acid) buffer, 100 U/ml penicillin G sodium and 100 μg/ml streptomycin sulfate. Stock cultures were maintained at 37° C. in a humidified 5% $CO_2$ incubator.

Reagents

FBS and Lipofectin (liposome formulation of the cationic lipid N-[1-(2,3-dioleyloxy)propyl]-n,n,n-trimethylammonium chloride) were purchased from Invitrogen (Grand Island, N.Y.). The anti-bcl-2 monoclonal antibody was from Dako (Carpinteria, Calif.). The anti-α-tubulin monoclonal antibody and 3-(4,5-dimethylthiazol-2-yl)-2,5-diphenyltetrazolium bromide ("MTT") were purchased from Sigma-Aldrich (St. Louis, Mo.). Phosphorothioate oligonucleotides were synthesized and purified via standard procedures.

Oligonucleotide Transfection

Cells were seeded the day before the experiment in 6-well plates at a density of 25×104 cells per well, to be 60-70% confluent on the day of the experiment. All transfections were performed in Opti-MEM medium in the absence of FBS and antibiotics as per the manufacturer's instructions. The appropriate quantities of reagents were diluted in 100 μl of Opti-MEM medium to give a final concentration of Lipofectin and oligonucleotide. The solutions were mixed gently and preincubated at room temperature for 30 minutes to allow complexes to form. Then, 800 μl of Opti-MEM was added, the solution mixed, and overlaid on the cells that had been prewashed with Opti-MEM. The incubation time for oligonucleotide/Lipofectin complexes in Opti-MEM was 24 hrs, followed by incubation in complete media containing 10% FBS. The total incubation time before cell lysis and protein isolation was usually 72 h at 37° C.

Western Blot Analysis

Cells treated with oligonucleotide-lipid complexes were washed in PBS and then extracted in lysis buffer [50 mM Tris-HCl pH 7.4, 1% NP-40, 0.25% sodium deoxycholate, 150 mM NaCl, 1 mM EGTA, 50 μg/ml Pefabloc SC, 15 μg/ml aprotinin, leupeptin, chymostatin, pepstatin A, 1 mM Na3VO4, 1 mM NaF] at 4° C. for 1 h. Cell debris was removed by centrifugation at 14 000 g for 20 rain at 4° C. Protein concentrations were determined using the Bio-Rad protein assay system (Bio-Rad Laboratories, Richmond, Calif.). Aliquots of cell extracts, containing 25-40 μg of protein, were resolved by SDS-PAGE, and then transferred to Hybond ECL filter paper (Amersham, Arlington Heights, Ill.), and the filters incubated at room temperature for 1-2 hr in 5% BSA in PBS containing 0.5% Tween-20. The filters were then probed with 1:500 dilutions of the anti bcl-2 antibody in 5% BSA in PBS containing 0.5% Tween-20 at 4° C. overnight. After washing in PBS containing 0.5% Tween-20, the filters were incubated for 1 hour at room temperature in 5% milk in PBS containing 0.5% Tween with a 1:3,000 dilution of a peroxidase-conjugated secondary antibody (Amersham). After washing (3×10 min), electrochem-iluminescense ("ECL") was performed according to the manufacturer's instructions.

Determination of Rate of Cell Proliferation

The effect on cellular viability of PEG conjugates was determined by MTT assay. Briefly, 15-20×$10^4$ cells were seeded in 6-well plates and allowed to attach overnight. Cells were then treated with the appropriate concentrations of oligonucleotide complexed to Lipofectin for 24 hrs at 37° C., followed by incubation in complete media (100 μl) containing 10% FBS. Cell viability was determined daily. Ten μl of 5 mg/ml MTT in PBS was added to each well, followed by incubation for 4 h at 37° C. Then, 100 μl of 10% SDS in 0.04 M HCl was added to each well, followed by incubation for overnight at 37° C. to dissolve the formazan crystals. Absorbance was determined at 570 mn with a Benchmark plus Microplate spectrophotometer (Bio Rad, Hercules, Calif.). Experiments were performed in 6 replicates, and data are presented as the average +/− S.D.

Quantitation of Intracellular ROS Levels

2',7'-dichlorodihydrofluorescein diacetate ($H_2$DCF-DA) and dihydroethidium (HE) were used to determined reactive oxygen species ("ROS") and superoxide levels. Both dyes are nonfluorescent and can freely diffuse into cells. When HE is oxidized to ethidium (E), it intercalates into cellular DNA and fluoresces. Oxidation of $H_2$DCF-DA yields 2'-7' dichlorofluorescein (DCF), which also fluoresces, and both can be detected by flow cytometry. Cells were harvested by trypsinization, washed with PBS and stained with 50 µM $H_2$DCF-DA or 50 µM HE in phenol red-free DMEM for 2 h at 37° C. The mean fluorescence channel numbers of DCF and E were analyzed by flow cytometry in the FL-1 and FL-2 channels respectively. A minimum of 10,000 cells were acquired for each sample and data were analyzed using CELLQuest software (Becton Dickinson). Histograms were plotted on a logarithmic scale.

Example 22

Inhibition Of Bcl-2 Protein Expression

Three PEG oligonucleotides (compounds 14, 28 and 33) targeted to bcl-2 expression were transfected into PC3 cells and their capacity to inhibit bcl-2 protein expression was evaluated by Western blotting.

Effects of Lipofectin

Figure 12:
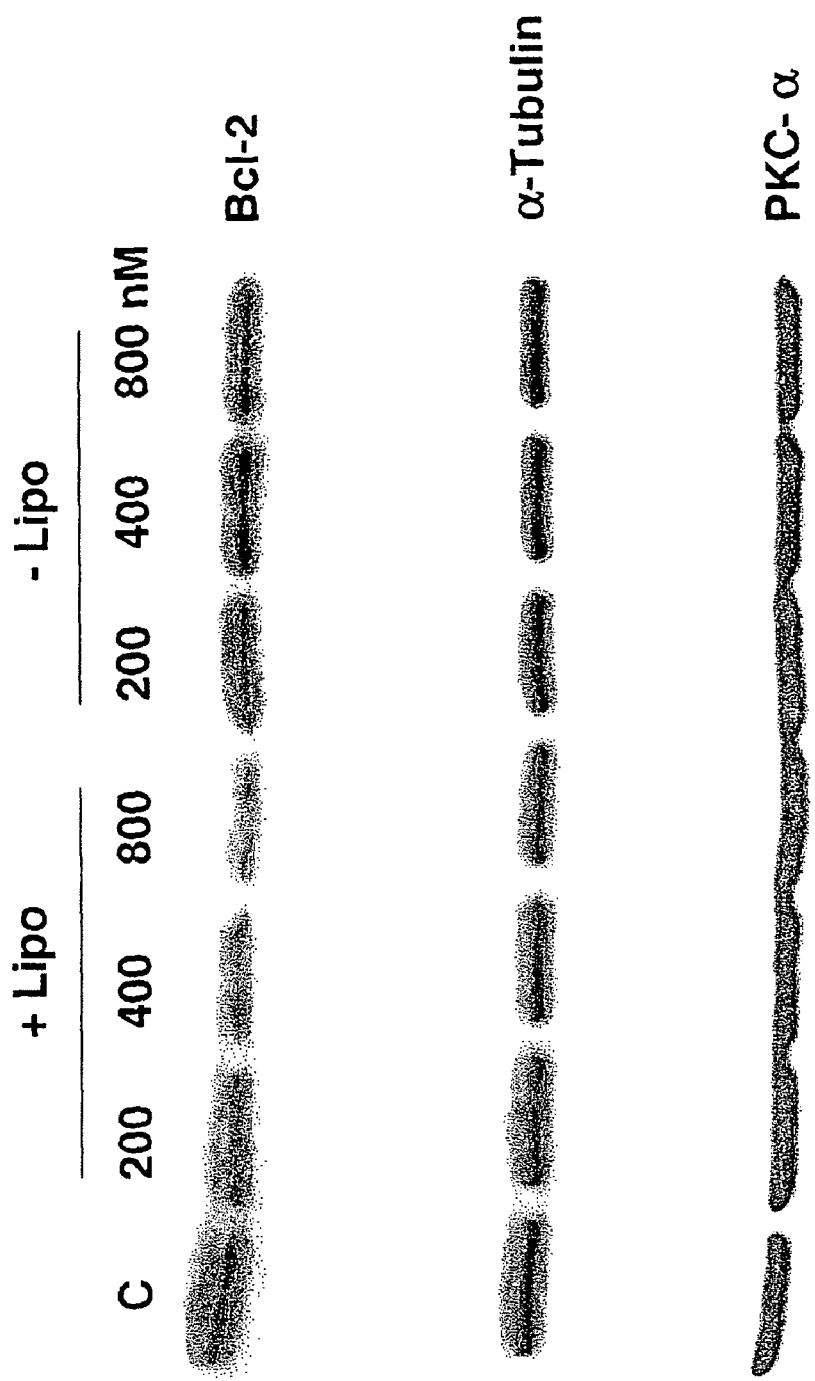
FIG. 12 is a Western Blot results confirming inhibition of bcl-2 protein expression by compound 14 in the presence of Lipofectin. PC3 cells were treated with compound 14 oligonucleotide (200, 400 and 800 nM) in the presence (+Lipo) and absence (−Lipo) of Lipofectin for 24 hrs in Opti-MEM, and then for a further 67 hrs in complete media. Protein samples (30-40 µg of protein/lane) were analyzed by Western blotting as described in the Material and Methods, with tubulin used as a control protein species. "C" marks the control.

Initially, the degree of inhibition of bcl-2 protein expression in PC3 cells induced by compound 14 was determined in the presence and absence of Lipofectin. PC3 cells were treated with compound 14 (at 200, 400 and 800 nM) in the presence or absence of Lipofectin for 24 hrs in Opti-MEM, and then for a further 67 hrs in complete media. Protein samples (30-40 µg of protein/lane) were analyzed by Western blotting as described in the Material and Methods, with tubulin used as a control protein species. The % inhibition vs. control, untreated cells was determined by laser-scanning densitometry. The Western Blot results are shown by FIG. 12.

The expression of α-tubulin and PKC-α was unchanged, confirming that Lipofectin is helpful to obtaining penetration of compound 14 into PC-3 cells, and confirming that only bcl-2 protein expression was downregulated by compound 14.

Further investigation demonstrated that compounds 14 and 28 were the most active at 400 nM. PC3 cells were treated with complexes of compound 14, compound 28, and compound 23 at 400, 800 and 1000 nM and Lipofectin for 24 hrs in Opti-MEM, and then for a further 67 hrs in complete media. Protein samples (30-40 µg of protein/lane) were analyzed by Western blotting as described in the Material and Methods, with tubulin used as a control protein species. The % inhibition vs. control, untreated cells was determined by laser-scanning densitometry.

Compound 14 produced 86% downregulation and compound 28 produced 78% downregulation.

Example 23

Dose-dependent Analysis of bcl-2 Protein Expression by PEG Oligonucleotides

To further confirm the inhibitory effect of compounds 14 and 28 on bcl-2 protein expression, PC3 cells were treated with increasing concentrations (25, 50, 100, 200 and 400 nM) of compound 14, compound 28, and compound 13 as a positive control, complexed to Lipofectin, for 24 hrs in Opti-MEM, and then for a further 67 hrs in complete media. Protein samples (30-40 µg of protein/lane) were analyzed by Western blotting as described in the Material and Methods section, supra.

A concentration-dependent inhibition of bcl-2 protein expression was observed by Western Blot for compounds 14 and 28, relative to controls. About 1-2% inhibition was observed at 50 nM, increasing to 99% and 75% at a concentration of 400 nM. For compound 24, essentially no inhibition was observed at 50 nM, but the inhibition increased to 77% at a concentration of 400 nM. Transfection with compound 13 was used as a positive control. The expression of α-tubulin was not inhibited by any oligonucleotide.

The above experiment was repeated with compound 24 as a control. PC3 cells were treated with increased concentrations of compounds 35 and 24 (25, 50, 100, 200 and 400 nM) were complexed to Lipofectin for 24 hrs in Opti-MEM, and then for a further 67 hrs in complete media. Protein samples (30-40 µg of protein/lane) were analyzed by Western blotting as described in the Material and Methods section, supra, with α-tubulin used as a control protein species. The % inhibition vs. control, untreated cells was determined by laser-scanning densitometry.

Example 24

Effect of PEG Oligonucleotides on PC3 Cell Growth

Figure 10:
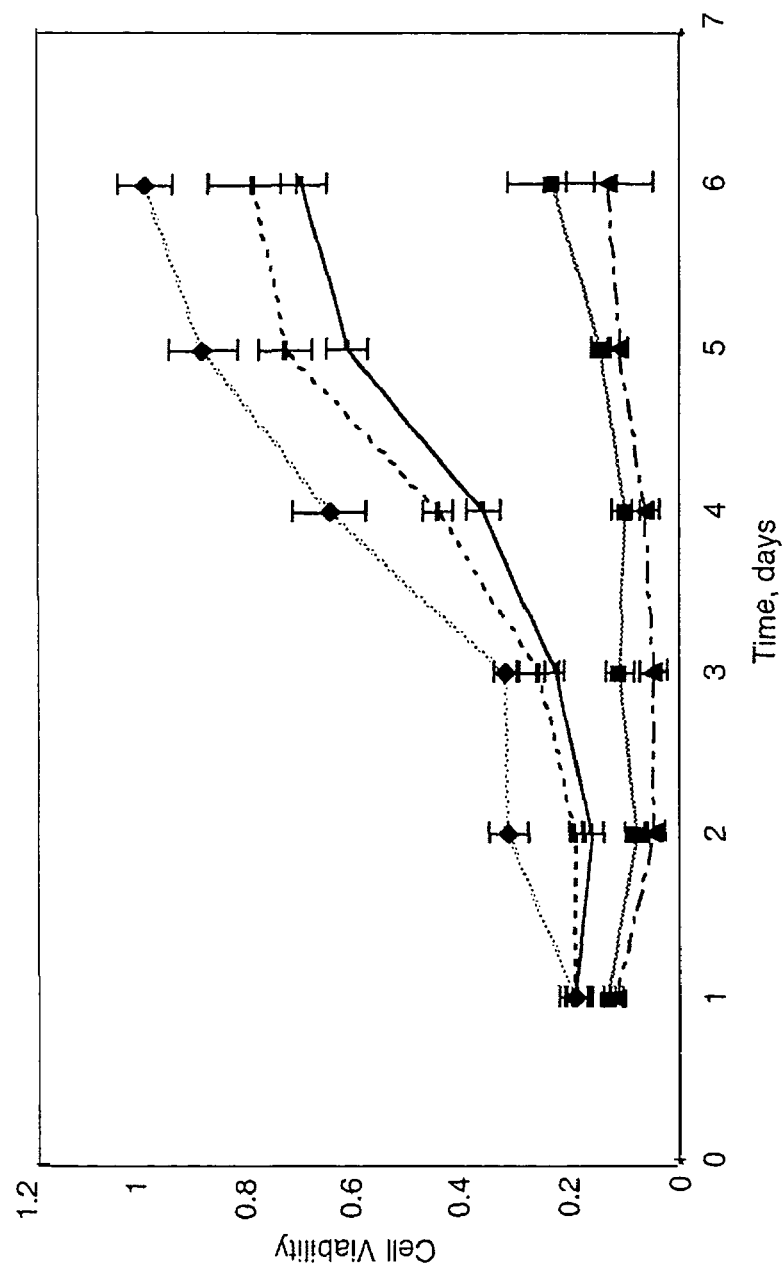
FIG. 10 illustrates the inhibitory effects of compound 14 and compound 28 on PC3 cell growth. $0.4 \times 10^4$ cells were seeded in 96-well plates, treated either with complexes of compound 14 or compound 28 (400 nM) and Lipofectin (15 µg/ml) for 24 hrs in Opti-MEM and then in complete media without complexes. Cellular viability was determined daily, and absorbances were measured at 570 nm. Data are presented as the average±standard deviation; n=4. Curves are as follows:
Control is marked by ◆ and a dotted curve;
Compound 28 at 400 nM is marked by ■ and a solid curve;
Compound 14 at 400 nM is marked by ▲ and a dashed curve;
Compound 28 at 200 nM is marked by ■ and a dashed curve;
Compound 14 at 200 nM is marked by ■ and a dotted curve.

The effects of compounds 14 and compound 28 on the growth of PC3 prostate cancer cells, in vitro, was also tested. PC3 cells were treated with oligonucleotide/Lipofectin complexes. As shown in FIG. 10, transfection of antisense oligonucleotide compound 14 at 400 and 200 nM strongly inhibited cell growth, while compound 28 only slightly affected the proliferation rate.

Example 25

Figure 11A:
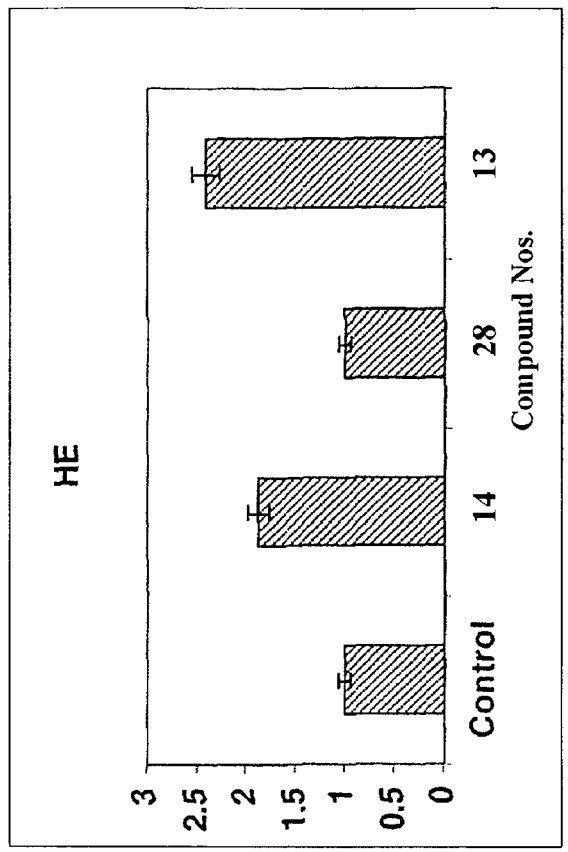
FIG. 11A provides a summary of ROS production (from flow cytometric analysis) by compound 14 and compound 28 oligonucleotides, by detecting the oxidation of cell-permeable 2',7'-dihydrodichlorofluorescein diacetate to fluorescent 2',7'-dichlorofluorescein (DCF). PC3 cells were treated with oligonucleotides (400 nM)/Lipofectin (15 µg/ml) complexes for 24 hrs, and assayed after 3 days, as described. Fold increases in mean fluorescence channel were normalized against untreated cells. Experiments were done in triplicate and data are presented as mean±standard deviation (n=3).
Figure 11B:
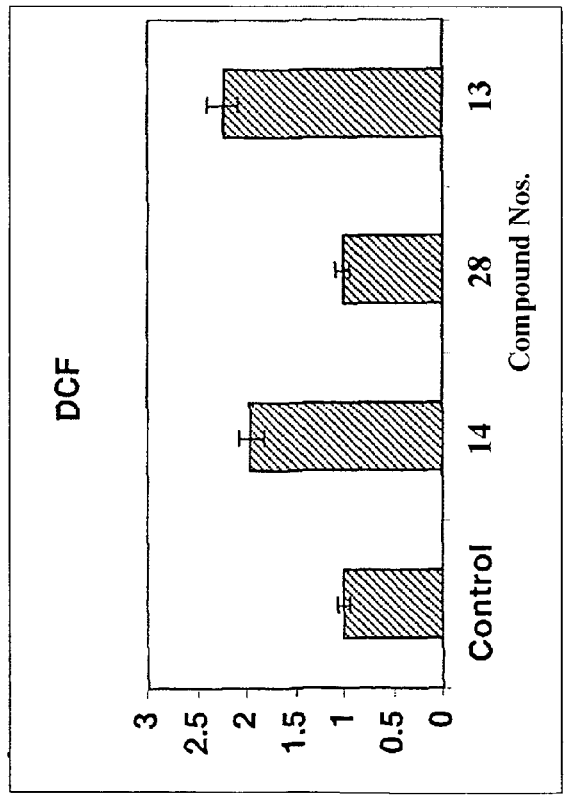
FIG. 11B provides a summary of ROS production (from flow cytometric analysis) by compound 14 and compound 28 oligonucleotides, by detecting the oxidation of hydroethidium (HE) to ethidium (E), which subsequently intercalates into DNA with fluorescence detectable by flow cytometry. PC3 cells were treated with oligonucleotides (400 nM)/Lipofectin (15 µg/ml) complexes for 24 hrs, and assayed after 3 days, as described. Fold increases in mean fluorescence channel were normalized against untreated cells. Experiments were done in triplicate and data are presented as mean±standard deviation (n=3).

Effect of PEG Oligonucleotides on Production of Reactive Oxygen Species in PC3 Cells Production of reactive oxygen species or ROS in PC3 cells was evaluated flow cytometrically by two methods. The first was based on oxidation of hydroethidium (HE) to ethidium (E), which subsequently intercalates into DNA with fluorescence detectable by flow cytometry. The second method employed the oxidation of cell-permeable 2',7'-dihydrodichlorofluorescein diacetate to fluorescent 2',7'-dichlorofluorescein (DCF). In PC3 cells, treatment with compound 14/Lipofectin (400 nM/15 µg/ml) complexes for 24 hours in Opti-MEM generated ROS three days later as evaluated by flow cytometrically by both E (1.9-fold increase vs. control, untreated cells) and DCF (2-fold increase vs. control, untreated cells) fluorescence. As confirmed by the data summarized by FIG. 11, compound 28 did not produced any increase in ROS production vs. control, untreated cells. Furthermore, the production of ROS is very closely linked to the rate of cellular proliferation; cells cease growing after treatment with 400 nM of compound 14, and this oligonucleotide also causes an increase in the production of ROS (DCF and HE).

SEQUENCE LISTING

<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate backbone
<220> FEATURE:
<223> OTHER INFORMATION: see specification as filed for detailed
      description of linkages and preferred embodiments

<400> SEQUENCE: 1
tctcccagcg tgcgccat                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate backbone
<220> FEATURE:
<223> OTHER INFORMATION: see specification as filed for detailed
      description of linkages and preferred embodiments

<400> SEQUENCE: 2
tctcccagcg tgtgccat                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate backbone
<220> FEATURE:
<223> OTHER INFORMATION: see specification as filed for detailed
      description of linkages and preferred embodiments

<400> SEQUENCE: 3
atcctaagcg tgcgcctt                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate backbone
<220> FEATURE:
<221> NAME/KEY: modified_base
<222> LOCATION: (9)

```
<223> OTHER INFORMATION: 5-Me-dC
<220> FEATURE:
<221> NAME/KEY: modified_base
<222> LOCATION: (13)
<223> OTHER INFORMATION: 5-Me-dC
<220> FEATURE:
<223> OTHER INFORMATION: see specification as filed for detailed
      description of linkages and preferred embodiments

<400> SEQUENCE: 4
tctcccagng tgngccat                                                       18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
taccgcgtgc gaccctc                                                        17

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagcgtgcgc catccttccc                                                     20

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cttttcctct gggaaggatg gcgcacgctg ggaga                                    35

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatgcaccta cccagcctcc                                                     20

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

```
                               -continued

<400> SEQUENCE: 9
acggggtacg gaggctgggt aggtgcatct ggt                              33

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acaaaggcat cctgcagttg                                             20

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cccccaactg caggatgcct ttgtggaact gtacgg                           36
```

e) Column 63, line 60, in claim 12,
"-SHCH₂CH₂-O-(CH₂CH₂O)ₙ'-CH₂CH₂SH-,"
should read -- -SCH₂CH₂-O-(CH₂CH₂O)ₙ'-CH₂CH₂S-, --.
f) Column 68, line 11, in claim 28,
The third compound
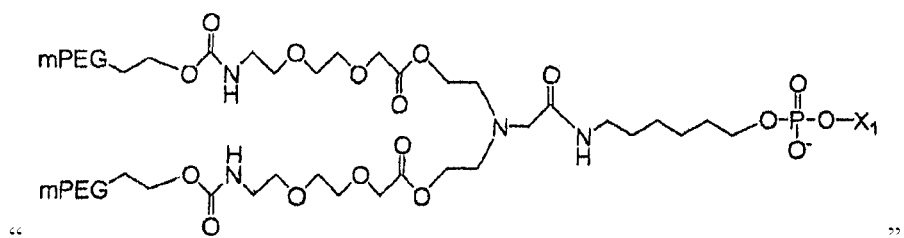
should have the structure
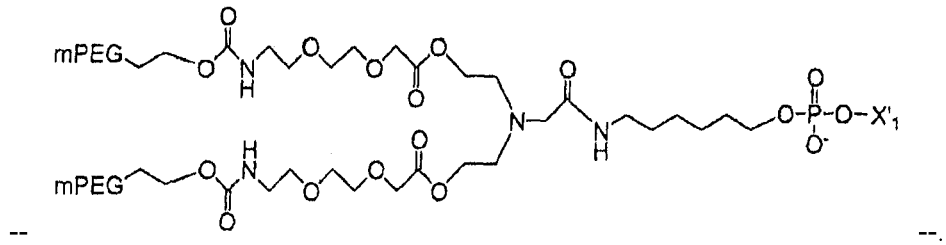
g) Column 68, line 11, in claim 28,
The fourth compound
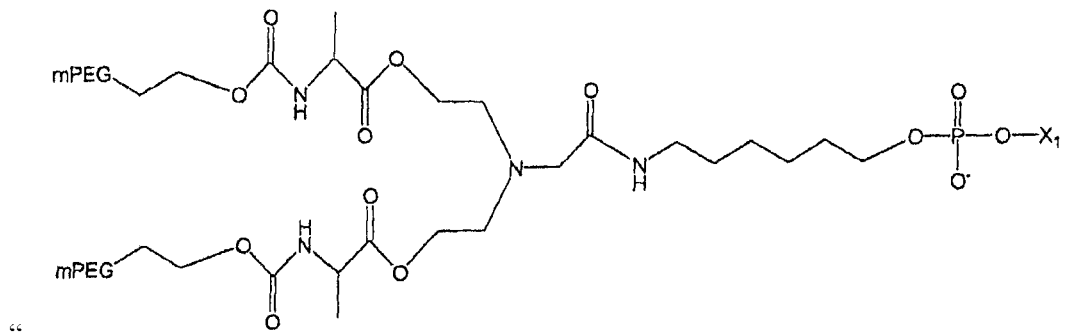

should have the structure
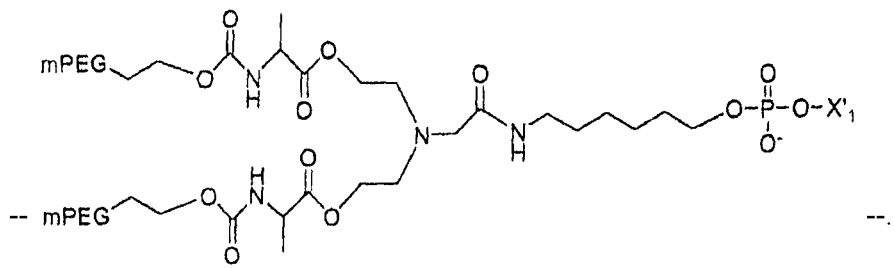

We claim:

1. An oligonucleotide prodrug of the formula:

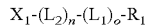

wherein:

$R_1$ is a polyalkylene oxide;

$L_1$ is a releasable linking moiety;

$L_2$ is a selected bifuntional spacing group comprising from about 2 to about 10 carbon atoms;

$X_1$ is a single or double stranded oligonucleotide residue wherein the oligonucleotide ranges in size from 10 to 1,000 nucleotides;

n, and o are independently a positive integer; and provided that $(o+n) \geq 2$, wherein $L_2$ is selected from the group consisting of:

—$(CR_{50'}R_{51'})_{q'}Q'$-,

—$(CR_{52'}R_{53'})_{r'}O(CR_{50'}R_{51'})_{q'}Q'$-,

—$(CR_{52'}R_{53'})_{r'}(OCH_2CH_2)Q'$-, and wherein

Q' is O, S or NH;

$R_{50'-53'}$ are independently selected from the group consisting of hydrogen, $C_{1-6}$ alkyls, $C_{3-12}$ branched alkyls, $C_{3-8}$ cycloalkyls, aryls, $C_{1-6}$ heteroalkyls, $C_{1-6}$ alkoxy, phenoxy and $C_{1-6}$ heteroalkoxy; and q' and r' are each a positive integer.

2. The prodrug of claim 1, wherein the oligonucleotide comprises a nucleotide that is selected from the group consisting of

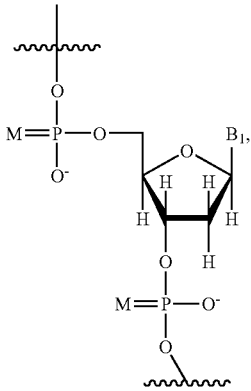

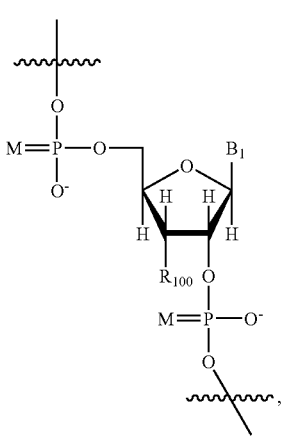

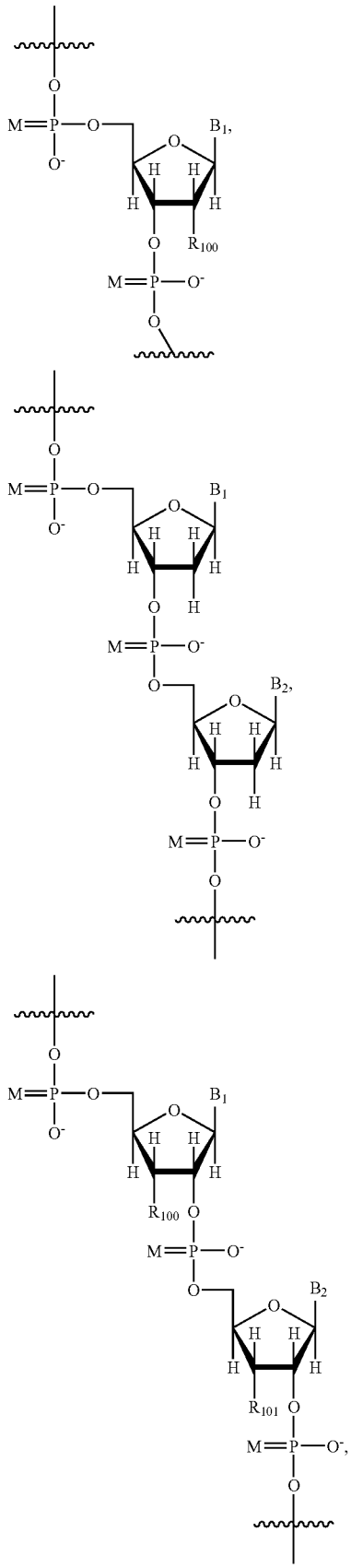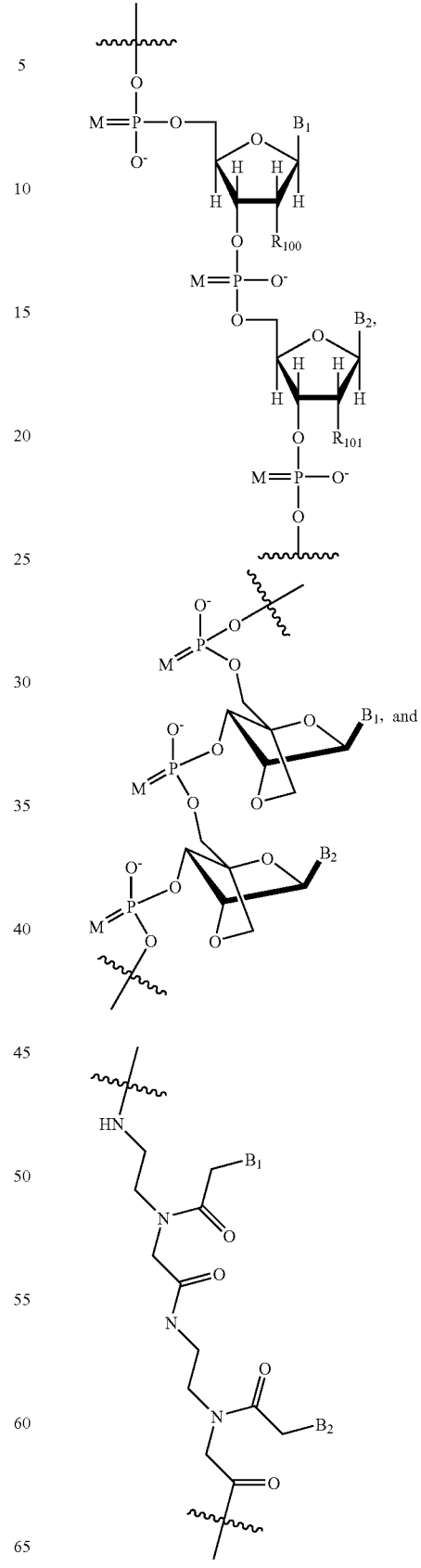

wherein

M is O or S;

$B_1$ and $B_2$ are independently selected from the group consisting of A (adenine), G (guanine), C (cytosine), T (thymine), U (uracil) and modified bases;

$R_{100}$ and $R_{101}$ are independently selected from the group consisting of H, OR' where R' is H, a $C_{1-6}$ alkyl, substituted alkyls, nitro, halo and aryl.

3. The prodrug of claim 2, wherein M is S.

4. The prodrug of claim 1, wherein the oligonucleotide residue is a phosphorothioate oligonucleotide residue.

5. The prodrug of claim 1, wherein said oligonucleotide residue is an antisense oligonucleotide residue or oligodeoxynucleotide residue.

6. The prodrug of claim 5, wherein said antisense oligonucleotide residue or oligodeoxynucleotide residue is selected from the group consisting of oligonucleotides and oligodeoxynucleotides with phosphorodiester backbones or phosphorothioate backbones, LNA, PNA, tricyclo-DNA, decoy ODN, ribozymes, spiegelmers, and CpG oligomers.

7. The prodrug of claim 5, wherein said antisense oligonucleotide has a sequence selected from the group consisting of SEQ ID NO: 1, SEQ ID NO: 2, SEQ ID NO: 3, and SEQ ID NO: 4, wherein n of SEQ ID NO: 4 is any nucleotide.

8. The prodrug of claim 1, wherein $R_1$ is a polyalklene oxide having a capping group A, selected from the group consisting of OH, $NH_2$, SH, $CO_2H$, $C_{1-6}$ alkyls, and $$X_2-(L_2)_n-(L_1)_o \quad (II)$$

wherein $X_2$ is a single stranded or double stranded oligonucleotide residues, wherein the oligonucleotide ranges in size from 10 to 1,000 nucleotides.

9. A prodrug of claim 8, selected from the group consisting of:

H—$X_1$—$(L_2)_n$—$(L_1)_o$—$R_1$—$(L_1)_o$—$(L_2)_n$—$X_2$—H wherein $X_2$ is a 3' oligonucleotide or 5' oligonucleotide.

10. The prodrug of claim 1, wherein $L_1$ is selected from the group consisting of:

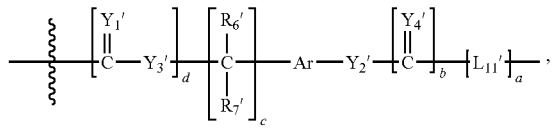

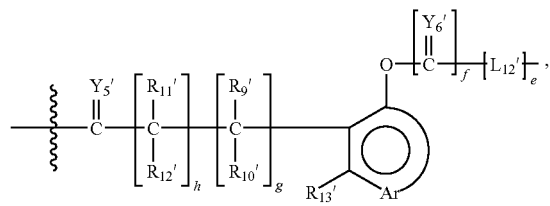

r

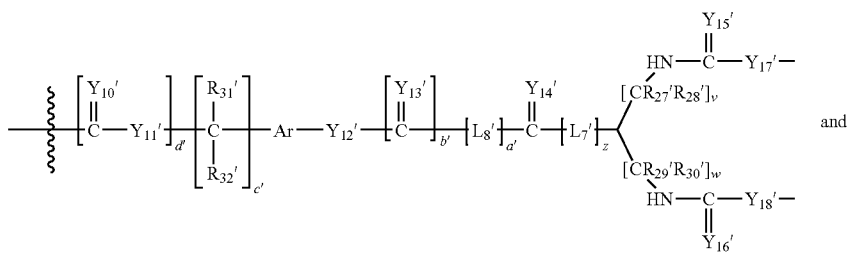

and

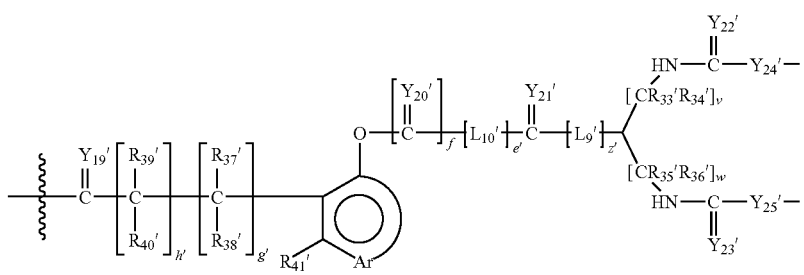

wherein, $Y_1\text{-}Y_{25'}$ are independently selected from the group consisting of O, S or $NR_9$;

$R_{6'\text{-}7'}$, $R_{9'\text{-}13'}$, $R_{16'\text{-}25'}$, $R_9$ and $R_{27'\text{-}41'}$ are independently selected from the group consisting of hydrogen, $C_{1-6}$ alkyls, $C_{3-12}$ branched alkyls, $C_{3-8}$ cycloalkyls, aryls, $C_{1-6}$ heteroalkyls, $C_{1-6}$ alkoxy, phenoxy and $C_{1-6}$ heteroalkoxy;

$L_{5'\text{-}12'}$ are independently selected bifunctional spacers;

Ar is a moiety which forms a multi-substituted aromatic hydrocarbon or a multi-substituted heterocyclic group;

c, h, k, l, r, s, v, w, v', w', c', and h' are independently selected positive integers;

a, e, g, j, t, z, a', z', e' and g' are independently either zero or a positive integer; and b, d, f, i, u, b', d' and f' are independently zero or one.

11. The prodrug of claim 1, wherein $R_1$ is a polyethylene glycol.

12. The prodrug of claim 1, wherein $R_1$ is selected from the group consisting of:

J—O—$(CH_2CH_2O)_{n'}$—

J—O—$(CH_2CH_2O)_{n'}$—$CH_2C(O)$—O—,

J—O—$(CH_2CH_2O)_{n'}$—$CH_2CH_2$ $NR_{48}$—,

J—O—$(CH_2CH_2O)_{n'}$—$CH_2CH_2$ SH,

—O—$C(O)CH_2$—O—$(CH_2CH_2O)_{n'}$—$CH_2C(O)$—O—,

—$NR_{48}CH_2CH_2$—O—$(CH_2CH_2O)_{n'}$—$CH_2CH_2$ $NR_{48}$—,

—$SHCH_2CH_2$—O—$(CH_2CH_2O)_{n'}$—$CH_2CH_2$ SH—, wherein n' is the degree of polymerization;

$R_{48}$ is selected from the group consisting of hydrogen, $C_{1-6}$ alkyls, $C_{3-12}$ branched alkyls, $C_{3-8}$ cycloalkyls, aryls, $C_{1-6}$ heteroalkyls, $C_{1-6}$ alkoxy, phenoxy and $C_{1-6}$ heteroalkoxy; and J is a capping group.

13. The prodrug of claim 1, wherein $R_1$ comprises

—O—$(CH_2CH_2O)_x$— wherein x is a positive integer selected so that the weight average molecular weight is at least about 2,000 Da to about 136,000 Da.

14. The prodrug of claim 1, wherein $R_1$ has a weight average molecular weight of from about 3,000 Da to about 100,000 Da.

15. The prodrug of claim 1, wherein $R_1$ has a weight average molecular weight of from about 5,000 Da to about 40,000 Da.

16. The prodrug of claim 7, wherein said antisense oligonucleotide is oblimersen (SEQ ID NO: 1).

17. A prodrug of claim 1 selected from the group consisting of:

—C—C—A—G—C—G—T—G—C—G—C—C—A—T;

and wherein all of which comprise an oligonucleotide of SEQ ID NO: 1.

18. A method of making a prodrug comprising:

reacting a compound of the formula:

$R_1\text{-}L_1\text{-leaving group}$ with a compound of the formula:

$H\text{-}L_2\text{-}X_1$ under conditions sufficient to form a prodrug of the formula $X_1\text{-}L_2\text{-}L_1\text{-}R_1$, wherein:

$R_1$ is a polyalkylene oxide;

$L_1$ is a releasable linking moiety;

$L_2$ is a bifunctional spacing group comprising from about 2 to about 10 carbon atoms; and $X_1$ is a single or double stranded oligonucleotide residue wherein the oligonucleotide ranges in size from 10 to 1,000 nucleotides, wherein $L_2$ is selected from the group consisting of —$(CR_{50'}R_{51'})_{q'}Q'$-,
—$(CR_{52'}R_{53'})_{r'}O(CR_{50'}R_{51'})_{q'}Q'$-,
—$(CR_{52'}R_{53'})_{r'}(OCH_2CH_2)Q'$-, and
—$(CH_2)_{r'}$—S—S—$(CH_2)_{q'}Q'$-, wherein $Q'$ is O, S or NH;

$R_{50'-53'}$ are independently selected from the group consisting of hydrogen, $C_{1-6}$ alkyls, $C_{3-12}$ branched alkyls, $C_{3-8}$ cycloalkyls, aryls, $C_{1-6}$ heteroalkyls, $C_{1-6}$ alkoxy, phenoxy and $C_{1-6}$ heteroalkoxy; and $q'$ and $r'$ are each a positive integer.

19. An oligonucleotide prodrug prepared by a process comprising:

reacting a compound of the formula:

$R_1$-$L_1$-leaving group with a compound of the formula:

H-$L_2$-$X_1$ under conditions sufficient to form a prodrug of the formula $X_1$-$L_2$-$L_1$-$R_1$, wherein $R_1$ is a polyalkylene oxide;

$L_1$ is a releasable linking moiety;

$L_2$ is a bifunctional spacing group comprising from about 2 to about 10 carbon atoms; and $X_1$ is a single or double stranded oligonucleotide residue wherein the oligonucleotide ranges in size from 10 to 1,000 nucleotides, wherein $L_2$ is selected from the group consisting of:

—$(CR_{50'}R_{51'})_{q'}Q'$-,
—$(CR_{52'}R_{53'})_{r'}O(CR_{50'}R_{51'})_{q'}Q'$-,
—$(CR_{52'}R_{53'})_{r'}(OCH_2CH_2)Q'$-, and
—$(CH_2)_{r'}$—S—S—$(CH_2)_{q'}Q'$-, wherein $Q'$ is O, S or NH;

$R_{50'-53'}$ are independently selected from the group consisting of hydrogen, $C_{1-6}$ alkyls, $C_{3-12}$ branched alkyls, $C_{3-8}$ cycloalkyls, aryls, $C_{1-6}$ heteroalkyls, $C_{1-6}$ alkoxy, phenoxy and $C_{1-6}$ heteroalkoxy; and $q'$ and $r'$ are each a positive integer.

20. The prodrug of claim 19, wherein $X_1$ comprises a nucleotide selected from the group consisting of

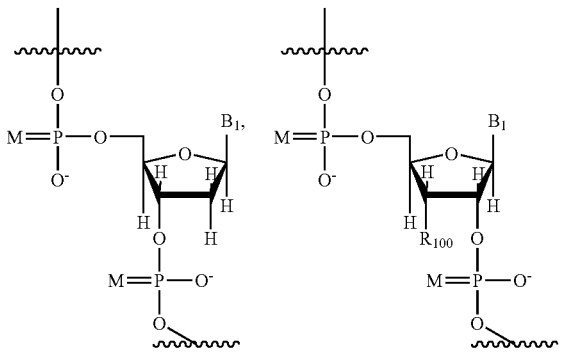

-continued

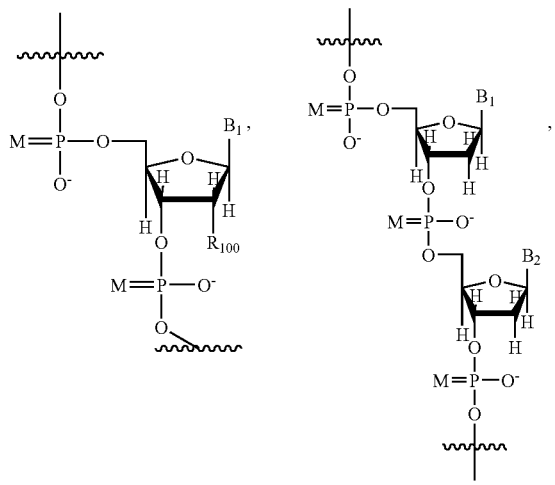

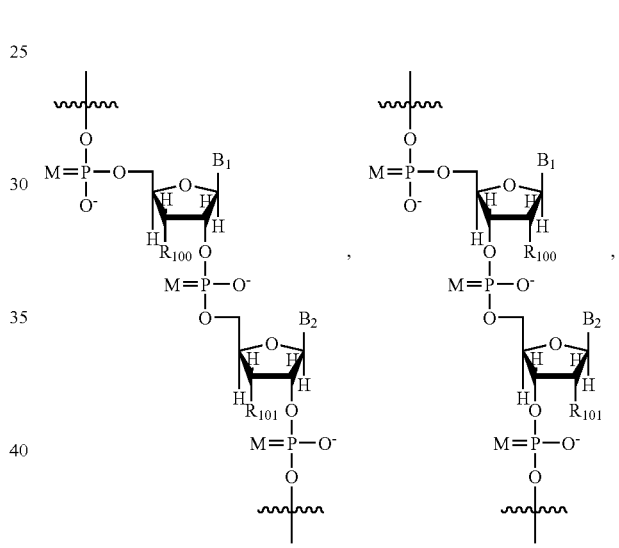

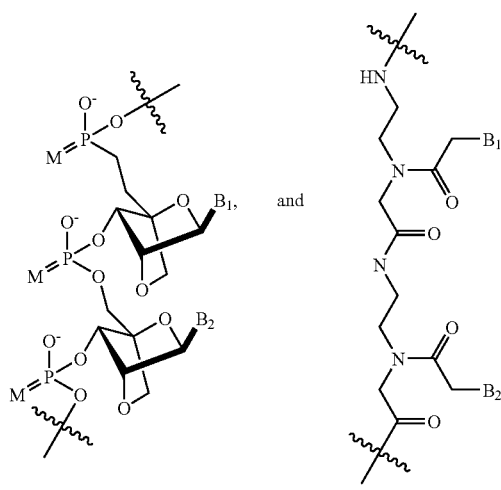

and wherein

M is O or S;

$B_1$ and $B_2$ are independently selected from the group consisting of A (adenine), G (guanine), C (cytosine), T (thymine), U (uracil) and modified bases thereof;

$R_{100}$ and $R_{101}$ are independently selected from the group consisting of H, OR' where R' is H, a $C_{1-6}$ alkyl, substituted alkyls, nitro, halo and aryl.

21. The prodrug of claim 19, wherein $X_1$ is selected from the group consisting of oligonucleotides with phosphorodiester backbones or phosphorothioate backbones, LNA, PNA, tricyclo-DNA, decoy ODN, ribozymes, spiegelmers, and CpG oligomers.

22. The prodrug of claim 19, wherein $X_1$ includes a phosphorothioate backbone.

23. The prodrug of claim 19, wherein $X_1$ is an antisense oligonucleotide.

24. The prodrug of claim 23, wherein the antisense oligonucleotide has a sequence selected from the group consisting of SEQ ID NO: 1, SEQ ID NO: 2, SEQ ID NO: 3, and SEQ ID NO: 4, wherein n of SEQ ID NO: 4 is any nucleotide.

25. The prodrug of claim 19, wherein $R_1$ is a polyalkylene glycol.

26. The prodrug of claim 19, wherein $R_1$ has a weight average molecular weight of from about 3,000 Da to about 100,000 Da.

27. The prodrug of claim 25, wherein $R_1$ has a weight average molecular weight of from about 5,000 Da to about 40,000 Da.

28. The prodrug of claim 19 selected from the group consisting of

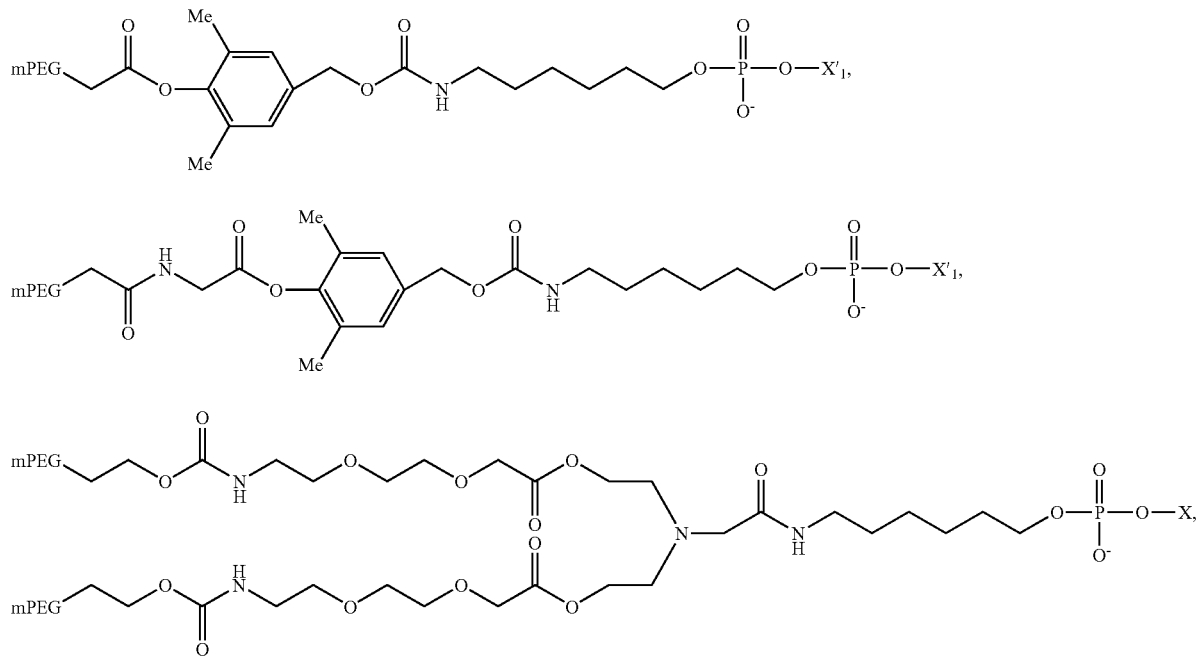

and

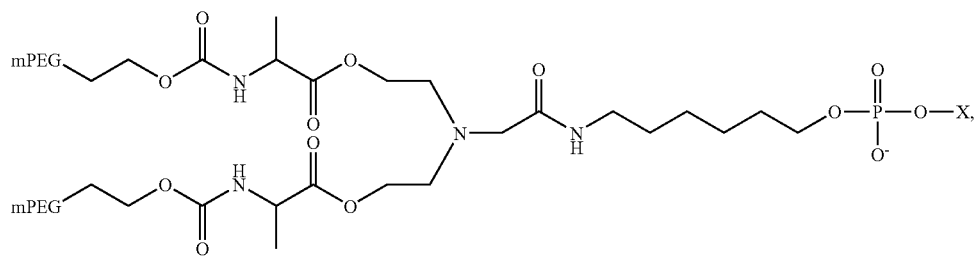

wherein

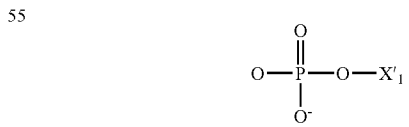

represents an oligonucleotide and point of terminal phosphate modification; and mPEG is $CH_3O(CH_2CH_2O)_x$-, wherein x is a positive integer selected from about 10 to about 2300.

* * * * *

UNITED STATES PATENT AND TRADEMARK OFFICE
CERTIFICATE OF CORRECTION

PATENT NO. : 7,595,304 B2  Page 1 of 3
APPLICATION NO. : 10/822205
DATED : September 29, 2009
INVENTOR(S) : Hong Zhao and Richard B. Greenwald It is certified that error appears in the above-identified patent and that said Letters Patent is hereby corrected as shown below:

Please correct the following:

a)  Column 57, lines 55-56 in claim 1, insert -- -$(CH_2)_{r'}$-S-S-$(CH_2)_{q'}Q'$-, -- between "and" and "wherein".

b)  Column 62, line 7 in claim 8,

"polyalklene" should read -- polyalkylene --.

c)  Column 62, lines 21-22 in claim 10,

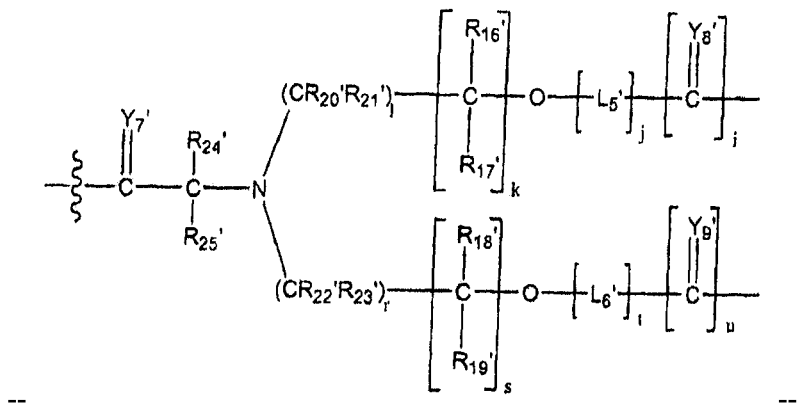

--                                                                    --

The above formula should be inserted between the second and third formula.

d)  Column 63, line 56 in claim 12,

"J-O-$(CH_2CH_2O)_{n'}$-$CH_2CH_2SH$-,"

should read -- J-O-$(CH_2CH_2O)_{n'}$-$CH_2CH_2S$-, --.